United States Patent
Levy et al.

(10) Patent No.: US 9,732,143 B2
(45) Date of Patent: Aug. 15, 2017

(54) METHODS AND MATERIALS FOR ENHANCING FUNCTIONAL PROTEIN EXPRESSION IN BACTERIA

(75) Inventors: Raphael D. Levy, Alameda, CA (US); Chung-Leung Chan, Sammamish, WA (US); Kiranjit K. Ahluwalia, Fremont, CA (US); Toshihiko Takeuchi, Oakland, CA (US)

(73) Assignee: XOMA TECHNOLOGY LTD., Berkeley, CA (US)

( * ) Notice: Subject to any disclaimer, the term of this patent is extended or adjusted under 35 U.S.C. 154(b) by 633 days.

(21) Appl. No.: 13/982,669

(22) PCT Filed: Feb. 3, 2012

(86) PCT No.: PCT/US2012/023801
§ 371 (c)(1),
(2), (4) Date: Feb. 14, 2014

(87) PCT Pub. No.: WO2012/106615
PCT Pub. Date: Aug. 9, 2012

(65) Prior Publication Data
US 2014/0154743 A1 Jun. 5, 2014

Related U.S. Application Data

(60) Provisional application No. 61/439,232, filed on Feb. 3, 2011.

(51) Int. Cl.
| | | |
|---|---|---|
| C07K 16/00 | (2006.01) | |
| C07K 14/245 | (2006.01) | |
| C12N 9/90 | (2006.01) | |
| C12N 15/67 | (2006.01) | |
| C07K 14/005 | (2006.01) | |

(52) U.S. Cl.
CPC ............ *C07K 16/00* (2013.01); *C07K 14/005* (2013.01); *C07K 14/245* (2013.01); *C12N 9/90* (2013.01); *C12N 15/67* (2013.01); *C12Y 502/01008* (2013.01); *C07K 2319/00* (2013.01); *C07K 2319/35* (2013.01)

(58) Field of Classification Search
CPC . C07K 2319/35; C12N 9/90; C12Y 502/1008
See application file for complete search history.

(56) References Cited

U.S. PATENT DOCUMENTS

| | | | | |
|---|---|---|---|---|
| 7,244,819 B2* | 7/2007 | Scholz | ............ | A61K 47/48246 530/350 |
| 2005/0106667 A1* | 5/2005 | Fellouse | ............ | C07K 16/005 435/69.1 |
| 2007/0160598 A1* | 7/2007 | Dennis | ............ | C07K 16/005 424/133.1 |
| 2007/0202552 A1* | 8/2007 | Sidhu | ............ | C07K 16/005 435/7.23 |
| 2007/0237764 A1* | 10/2007 | Birtalan | ............ | C07K 14/70503 424/133.1 |
| 2007/0243583 A1* | 10/2007 | Georgiou | ............ | C12N 9/90 435/69.1 |
| 2008/0254511 A1* | 10/2008 | Dassler | ............ | C07K 14/245 435/69.4 |
| 2009/0269338 A1* | 10/2009 | Huang | ............ | C07K 16/18 424/133.1 |
| 2011/0281300 A1* | 11/2011 | Lee | ............ | C12N 15/67 435/69.3 |

FOREIGN PATENT DOCUMENTS

| | | |
|---|---|---|
| WO | WO 03/000877 A2 | 1/2003 |
| WO | WO 2006/078273 A2 | 7/2006 |

OTHER PUBLICATIONS

Ramm, K., et al., 2001, "High enzymatic activity and chaperone function are mechanistically related features of the dimeric *E. coli* peptidyl-prolyl-isomerase FkpA", Journal of Molecular Biology, vol. 310, No. 2, pp. 485-498.*
Walton, T.A., et al., 2009, "The cavity-chaperone Skp protects its substrate from aggregation but allows independent folding of substrate domain", Proceedings of the National Academy of Sciences, USA, vol. 106, No. 6, pp. 1772-1777.*
Ieva, R., et al., 2009, "Interaction of an autotransporter passenger domain with BamA during its translocation across the bacterial outer membrane", Proceedings of the National Academy of Sciences, USA, vol. 106, No. 45, pp. 19120-19125.*
Arie, J.-P., et al., 2001, "Chaperone function of FkpA, a heat shock prolyl isomerase, in the periplasm of *Escherichia coli*", Molecular Microbiology, vol. 39, No. 1, pp. 199-210.*
Singh et al., Effect of Signal Peptide on Stability and Folding of Escherichia coli Thioredoxin, PLoS One, 2013, 8(5): e63442. doi:10.1371/journal.pone.0063442.*
Arbabi-Ghahroudi et al., Prokaryotic expression of antibodies, Cancer and Metastasis Reviews 24:501-19 (2005).
ATCC Product Sheet, pAR3 ATCC 87026, 2013.
Baneyx et al., Recombinant protein folding and misfolding in *Escherichia coli*, Nature Biotechnology, 22:1399-408 (2004).

(Continued)

*Primary Examiner* — Suzanne M Noakes
(74) *Attorney, Agent, or Firm* — Marshall, Gerstein & Borun LLP

(57) ABSTRACT

Novel materials and methods useful for expressing heterologous proteins in prokaryotic cells are provided, including prokaryotic cells expressing FkpA and/or Skp.

28 Claims, 29 Drawing Sheets

(56) References Cited

OTHER PUBLICATIONS

Bothman et al., Selection for a periplasmic factor improving phage display and functional expression, *Nature Biotechnology*, 16:376:380 (1998).

Bothmann et al., The Periplasmic *Escherichia coli* Peptidylprolylcis,trans-lsomerase FkpA, *J. Biol. Chem.*, 275(22): 17100-17105 (2000).

de Marco et al., Chaperone-based procedure to increase yields of soluble recombinant proteins produced in *E. coli*, *BMC Biotechnology*, 7:32 (2007).

de Marco, Strategies for successful recombinant expression of disulfide bond-dependent proteins in *Escherichia coli*, *Microbial Cell Factories*, 8:26 (2009).

Demain, Microbial biotechnology, *Trends in Biotech.*, 18(1):26-31 (2000).

Deshayes et al, Rapid identification of small binding motifs with high-throughput phage display: discovery of peptidic antagonists of IGF-1 function, *Chem. & Biol.*, 9:495-505 (2002).

Gebauer et al., Engineered protein scaffolds as next-generation antibody therapeutics, *Curr. Opin. Chem. Biol.*, 13:245-55 (2009).

Gill et al., Biopharmaceutical drug discovery using novel protein scaffolds, *Curr. Opin. Biotech.*, 17:653-8 (2006).

Hakim et al., "Inclonals": IgGs and IgG-enzyme fusion proteins produced in an *E. coli* expression-refolding system, *MAbs*, 1(3):281-7 (2009).

Hayhurst et al., *Escherichia coli* Skp chaperone coexpression improves solubility and phase display of single-chain antibody fragments, *Prot. Expres. Purif.*, 15(3):336-43 (1999).

Hosse et al., A new generation of protein display scaffolds for molecular recognition, *Protein Sci.*, 15:14-27 (2006).

Kolaj et al., Use of folding modulators to improve heterologous protein production in *Escherichia coli*, *Biomed Central*, 8(1):9 (2009).

Levy et al., Production of correctly folded Fab antibody fragment in the cytoplasm of *Escherichia coli trxB gor* mutants via the coexpression of molecular chaperones, *Protein Expr. Purif.*, 23(2):338-47 (2001).

Loset et al., Functional phage display of two murine a/b T-cell receptors is strongly dependent on fusion format, mode and periplasmic folding assistance, *Protein Engineering, Design & Selection*, 20(9):461-72 (2007).

Misawa et al., Refolding of therapeutic proteins produced in *Escherichia coli* as inclusion bodies, *Biopolymers*, 51:297-307 (1999).

Ow et al., Co-expression of Skp and FkpA chaperones improves cell viability and alters the global expression of stress response genes during scFvD1.3 production, *Microbial Cell Factories*, 9:22 (2010).

Paluh et al., High level production and rapid purification of the *E. coli* trp repressor, *Nucl. Acids Res.*, 14(20):7851-60 (1986).

Perez-Perez et al, An arabinose-inducible expression vector, pAR3, compatible with ColE1-derived plasmids, *Gene*,158(1):141-2 (1995).

Ramm et al., The periplasmic *Escherichia coli* peptidylprolyl cis,trans-isomerase FkpA. II. Isomerase-independent chaperone activity in vitro, *J. Biol. Chem.*, 275(22):17106-13 (2000).

Saul et al., Structural and functional studies of FkpA from *Escherichia coli*, a cis/trans peptidyl-prolyl isomerase with chaperone activity, *J. Mol. Bio.*, 335:595-608 (2004).

Schaffner et al., Cosecretion of chaperones and low-molecular-size medium additives increases the yield of recombinant disulfide-bridged proteins, *Appl. Environ. Microbiol.*, 67(9):3994-4000 (2001).

Sharma et al., Preparation of electrocompetent *E. coli* using salt-free growth medium, *Biotechniques*, 20:42-4 (1996).

Sidhu et al, Phage-displayed antibody libraries of synthetic heavy chain complementarity determining regions, *J. Molec. Biol.*, 338:299-310 (2004).

Skerra, Alternative non-antibody scaffolds for molecular recognition, *Curr. Opin. Biotech.*, 18:295-304 (2007).

Skretas et al., Expression of active human sialyltransferase ST6Ga1NAcl in *Escherichia coli*, *Microbial Cell Factories*, 8(1):50 (2009).

Song et al, Efficacious recombinant influenza vaccines produced by high yield bacterial expression: a solution to global pandemic and seasonal needs, *PLoS One*, 3(5):e2257 (2008).

Sonoda et al., Effects of cytoplasmic and periplasmic chaperones on secretory production of single-chain Fv antibody in *Escherichia coli*, *J. Biosci. Bioeng.*, 111(4):465-70 (2011).

SwissProt No. P0AEU7, Chaperone protein Skp, dated Dec. 20, 2005.

SwissProt No. P65764, FKBP-type peptidyl-prolyl cis-trans isomerase FkpA, dated Oct. 11, 2004.

Vahedi et al., Functional expression of Bacillus anthracis protective antigen in *E. coli*, *Applied Biotech.*, 157(3):554-61 (2009).

Zhang et al, Expression, refolding, purification, molecular characterization, crystallization, and preliminary X-ray analysis of the receptor binding domain of human B7-2, *Protein Expr. Purif.,* 25(1):105-13 (2002).
International Preliminary Report on Patentability, PCT/US2012/023801, dated Aug. 6, 2013.
International Search Report and Written Opinion of the International Searching Authority, European Patent Office, PCT/US2012/023801, dated May 4, 2012.

* cited by examiner

Western Blot (reduced) developed with anti-V5 antibodies for detection of Skp

| LANE | 1 | 2 | 3 | 4 | 5 | 6 | 7 | 8 | 9 | 10 |
|---|---|---|---|---|---|---|---|---|---|---|
| sample | TG1 | TG1 | Skp(-) | Skp(-) | Skp(+) | Skp(+) | Skp-FkpA(-) | Skp-FkpA(-) | Skp-FkpA(+) | Skp-FkpA(+) |
| extract | periplasmic | cytoplasmic | periplasmic | cytoplasmic | periplasmic | cytoplasmic | periplasmic | cytoplasmic | periplasmic | cytoplasmic |

(-): without signal sequence
(+): with signal sequence

Western Blot (reduced) developed with anti-FLAG antibodies for detection of FkpA

| LANE | 1 | 2 | 3 | 4 | 5 | 6 | 7 | 8 | 9 | 10 |
|---|---|---|---|---|---|---|---|---|---|---|
| sample | TG1 | TG1 | FkpA(-) | FkpA(-) | FkpA(+) | FkpA(+) | Skp-FkpA(-) | Skp-FkpA(-) | Skp-FkpA(+) | Skp-FkpA(+) |
| extract | periplasmic | cytoplasmic | periplasmic | cytoplasmic | periplasmic | cytoplasmic | periplasmic | cytoplasmic | periplasmic | cytoplasmic |

(-): without signal sequence (+): with signal sequence

|   | 1 | 2 | 3 | 4 | 5 | 6 | 7 | 8 | 9 | 10 | 11 | 12 |
|---|---|---|---|---|---|---|---|---|---|----|----|----|
| A | 1.0 / 8.4e-02 | 1.0 / 7.8e-02 | 0.8 / 5.2e-02 | 1.3 / 0.1 | 0.6 / 4.9e-02 | 0.6 / 4.9e-02 | 0.6 / 5.1e-02 | 0.6 / 4.7e-02 | 0.6 / 4.9e-02 | 0.6 / 5.0e-02 | 0.6 / 5.2e-02 | 0.7 / 5.4e-02 |
| B | 0.9 / 7.4e-02 | 0.6 / 5.2e-02 | 0.6 / 4.7e-02 | 0.5 / 4.3e-02 | 0.5 / 4.4e-02 | 0.6 / 4.7e-02 | 0.6 / 4.7e-02 | 0.6 / 4.6e-02 | 0.6 / 4.6e-02 | 0.6 / 4.9e-02 | 0.7 / 5.4e-02 | 1.0 / 8.4e-02 |
| C | 1.1 / 9.2e-02 | 0.6 / 4.9e-02 | 0.6 / 4.9e-02 | 0.6 / 4.6e-02 | 0.5 / 4.4e-02 | 0.6 / 5.2e-02 | 0.6 / 4.9e-02 | 0.6 / 4.5e-02 | 0.6 / 5.0e-02 | 0.6 / 5.2e-02 | 0.5 / 4.4e-02 | 0.7 / 5.3e-02 |
| D | 0.8 / 6.3e-02 | 0.6 / 5.1e-02 | 0.6 / 4.7e-02 | 0.6 / 4.5e-02 | 1.4 / 0.1 | 0.6 / 4.7e-02 | 1.0 / 8.3e-02 | 0.6 / 4.7e-02 | 0.6 / 4.4e-02 | 0.5 / 4.3e-02 | 0.5 / 5.0e-02 | 0.6 / 5.2e-02 |
| E | 0.8 / 6.6e-02 | 0.6 / 5.0e-02 | 0.6 / 4.6e-02 | 0.6 / 5.0e-02 | 0.6 / 4.6e-02 | 0.6 / 4.7e-02 | 0.6 / 4.7e-02 | 0.6 / 4.9e-02 | 0.5 / 4.4e-02 | 0.6 / 4.9e-02 | 0.5 / 4.4e-02 | 0.6 / 4.5e-02 |
| F | 0.7 / 5.7e-02 | 0.6 / 4.5e-02 | 0.6 / 4.9e-02 | 0.6 / 5.2e-02 | 0.9 / 7.2e-02 | 0.6 / 4.8e-02 | 0.7 / 5.3e-02 | 0.7 / 4.8e-02 | 0.5 / 4.4e-02 | 0.6 / 4.6e-02 | 0.8 / 5.2e-02 | 0.6 / 4.3e-02 |
| G | 0.9 / 7.0e-02 | 0.6 / 5.0e-02 | 0.6 / 4.6e-02 | 0.7 / 5.5e-02 | 0.6 / 5.1e-02 | 0.5 / 4.4e-02 | 0.5 / 4.3e-02 | 0.5 / 4.4e-02 | 0.6 / 4.8e-02 | 0.7 / 5.4e-02 | 0.5 / 4.3e-02 | 0.5 / 4.2e-02 |
| H | 0.9 / 7.4e-02 | 0.9 / 7.2e-02 | 0.8 / 6.4e-02 | 0.5 / 4.9e-02 | 0.6 / 5.0e-02 | 0.6 / 5.2e-02 | 0.6 / 5.1e-02 | 0.6 / 5.0e-02 | 0.5 / 4.1e-02 | 0.6 / 5.2e-02 | 0.7 / 5.5e-02 | 6.3 / 0.5 |

*FIG. 10A*

|   | 1 | 2 | 3 | 4 | 5 | 6 | 7 | 8 | 9 | 10 | 11 | 12 |
|---|---|---|---|---|---|---|---|---|---|----|----|----|
| A | 1.0<br>8.4e-02 | 1.0<br>5.2e-02 | 2.4<br>0.1 | 0.9<br>4.5e-02 | 1.5<br>7.7e-02 | 1.0<br>4.9e-02 | 0.9<br>4.4e-02 | 0.9<br>4.6e-02 | 0.9<br>4.6e-02 | 1.9<br>9.7e-02 | 1.2<br>6.2e-02 | 1.6<br>8.1e-02 |
| B | 1.0<br>5.1e-02 | 1.0<br>5.1e-02 | 1.5<br>7.9e-02 | 1.4<br>7.1e-02 | 1.3<br>6.6e-02 | 1.6<br>8.3e-02 | 1.4<br>7.1e-02 | 0.9<br>4.5e-02 | 0.9<br>4.6e-02 | 1.2<br>6.4e-02 | 2.3<br>0.1 | 1.3<br>6.5e-02 |
| C | 0.9<br>4.4e-02 | 0.9<br>4.8e-02 | 1.6<br>8.1e-02 | 1.0<br>5.0e-02 | 0.9<br>4.6e-02 | 14.2<br>0.7 | 0.9<br>4.4e-02 | 0.9<br>4.5e-02 | 1.6<br>8.3e-02 | 1.1<br>5.6e-02 | 0.8<br>4.4e-02 | 1.1<br>5.5e-02 |
| D | 2.0<br>0.1 | 1.0<br>4.9e-02 | 1.0<br>4.9e-02 | 0.9<br>4.7e-02 | 0.9<br>4.7e-02 | 0.9<br>4.6e-02 | 1.3<br>6.9e-02 | 1.0<br>5.0e-02 | 0.9<br>4.8e-02 | 0.9<br>4.8e-02 | 1.0<br>5.0e-02 | 1.9<br>9.6e-02 |
| E | 1.1<br>5.5e-02 | 1.0<br>5.0e-02 | 1.0<br>5.0e-02 | 0.9<br>4.8e-02 | 1.2<br>6.4e-02 | 1.1<br>5.8e-02 | 0.8<br>4.3e-02 | 0.9<br>4.6e-02 | 0.9<br>4.5e-02 | 1.0<br>4.9e-02 | 1.1<br>5.6e-02 | 0.9<br>4.7e-02 |
| F | 1.8<br>9.4e-02 | 1.0<br>5.0e-02 | 1.0<br>5.3e-02 | 0.9<br>4.8e-02 | 1.1<br>5.5e-02 | 0.9<br>4.8e-02 | 1.0<br>4.9e-02 | 0.9<br>4.9e-02 | 0.9<br>4.7e-02 | 1.5<br>7.7e-02 | 1.2<br>6.0e-02 | 0.8<br>4.3e-02 |
| G | 1.0<br>5.2e-02 | 1.0<br>5.0e-02 | 0.9<br>4.8e-02 | 0.9<br>4.8e-02 | 2.0<br>0.1 | 0.9<br>4.6e-02 | 1.0<br>4.7e-02 | 1.1<br>5.5e-02 | 1.0<br>5.3e-02 | 1.0<br>5.2e-02 | 1.4<br>7.0e-02 | 0.8<br>4.3e-02 |
| H | 5.1<br>0.3 | 1.2<br>6.0e-02 | 1.9<br>9.5e-02 | 1.0<br>5.2e-02 | 5.8<br>0.3 | 1.3<br>6.8e-02 | 1.1<br>5.5e-02 | 1.1<br>5.5e-02 | 1.2<br>6.4e-02 | 1.0<br>5.2e-02 | 1.0<br>5.3e-02 | 11.4<br>0.6 |

*FIG. 10B*

|   | 1 | 2 | 3 | 4 | 5 | 6 | 7 | 8 | 9 | 10 | 11 | 12 |
|---|---|---|---|---|---|---|---|---|---|----|----|----|
| A | 0.9 / 7.9e-02 | 1.1 / 9.3e-02 | 1.0 / 8.5e-02 | 0.7 / 5.6e-02 | 0.6 / 5.3e-02 | 0.6 / 5.0e-02 | 3.6 / 0.3 | 0.5 / 4.7e-02 | 0.6 / 4.9e-02 | 1.7 / 0.1 | 0.7 / 5.8e-02 | 0.8 / 6.9e-02 |
| B | 0.9 / 7.6e-02 | 0.7 / 5.7e-02 | 0.7 / 5.9e-02 | 0.6 / 5.1e-02 | 0.5 / 4.6e-02 | 0.5 / 4.5e-02 | 7.3 / 0.6 | 0.5 / 4.4e-02 | 0.5 / 4.5e-02 | 7.8 / 0.7 | 7.9 / 0.7 | 4.9 / 0.4 |
| C | 0.8 / 7.1e-02 | 7.4 / 0.6 | 6.8 / 0.6 | 6.9 / 0.6 | 0.6 / 5.4e-02 | 7.4 / 0.6 | 0.5 / 4.4e-02 | 1.2 / 9.9e-02 | 0.5 / 4.4e-02 | 7.4 / 0.6 | 0.7 / 6.3e-02 | 0.8 / 6.5e-02 |
| D | 3.1 / 0.3 | 7.3 / 0.6 | 0.6 / 4.9e-02 | 0.6 / 4.8e-02 | 2.1 / 0.2 | 0.6 / 4.8e-02 | 7.5 / 0.6 | 0.5 / 4.6e-02 | 1.0 / 8.7e-02 | 0.7 / 6.0e-02 | 3.5 / 0.3 | 6.8 / 0.6 |
| E | 0.9 / 7.6e-02 | 1.2 / 9.9e-02 | 3.1 / 0.3 | 5.9 / 0.5 | 4.0 / 0.3 | 0.6 / 5.3e-02 | 0.7 / 6.0e-02 | 0.5 / 4.6e-02 | 0.5 / 4.6e-02 | 4.3 / 0.4 | 0.7 / 6.0e-02 | 0.5 / 4.6e-02 |
| F | 3.4 / 0.3 | 0.6 / 5.5e-02 | 7.1 / 0.6 | 7.4 / 0.6 | 7.0 / 0.6 | 6.8 / 0.6 | 0.5 / 4.6e-02 | 7.6 / 0.7 | 1.5 / 0.1 | 0.5 / 4.5e-02 | 7.5 / 0.6 | 0.6 / 4.9e-02 |
| G | 7.5 / 0.6 | 7.4 / 0.6 | 0.8 / 6.8e-02 | 7.4 / 0.6 | 0.7 / 6.1e-02 | 0.6 / 5.3e-02 | 0.5 / 4.6e-02 | 0.6 / 5.5e-02 | 0.5 / 4.6e-02 | 7.1 / 0.6 | 0.5 / 4.3e-02 | 0.5 / 4.5e-02 |
| H | 0.9 / 7.4e-02 | 1.1 / 9.2e-02 | 1.2 / 0.1 | 1.3 / 0.1 | 6.6 / 0.6 | 0.8 / 7.1e-02 | 0.7 / 5.9e-02 | 0.8 / 6.9e-02 | 0.5 / 4.6e-02 | 0.7 / 6.1e-02 | 0.7 / 6.1e-02 | 6.2 / 0.5 |

*FIG. 11A*

| | 1 | 2 | 3 | 4 | 5 | 6 | 7 | 8 | 9 | 10 | 11 | 12 |
|---|---|---|---|---|---|---|---|---|---|---|---|---|
| A | 1.0 / 6.8e-02 | 1.0 / 6.2e-02 | 11.3 / 0.7 | 0.7 / 4.6e-02 | 10.8 / 0.4 | 0.7 / 4.8e-02 | 1.2 / 7.8e-02 | 1.3 / 8.6e-02 | 0.7 / 4.8e-02 | 8.9 / 0.6 | 0.8 / 5.0e-02 | 5.8 / 0.4 |
| B | 0.9 / 6.0e-02 | 0.9 / 5.9e-02 | 10.6 / 0.7 | 9.8 / 0.6 | 0.9 / 6.2e-02 | 10.1 / 0.7 | 10.8 / 0.7 | 1.1 / 7.0e-02 | 0.7 / 7.0e-02 | 0.8 / 5.0e-02 | 9.5 / 0.6 | 0.9 / 6.0e-02 |
| C | 1.0 / 6.2e-02 | 1.9 / 0.1 | 10.1 / 0.7 | 0.8 / 5.1e-02 | 0.7 / 4.6e-02 | 2.3 / 0.1 | 0.7 / 4.5e-02 | 12.0 / 7.7e-02 | 12.0 / 7.7e-02 | 0.8 / 5.3e-02 | 0.7 / 4.4e-02 | 0.8 / 5.3e-02 |
| D | 10.3 / 0.7 | 1.3 / 8.3e-02 | 0.7 / 4.4e-02 | 0.7 / 4.5e-02 | 0.7 / 4.6e-02 | 0.7 / 4.5e-02 | 10.4 / 0.7 | 1.1 / 6.8e-02 | 1.1 / 6.8e-02 | 0.7 / 4.5e-02 | 0.8 / 5.1e-02 | 10.9 / 0.7 |
| E | 0.9 / 5.7e-02 | 4.2 / 0.3 | 0.7 / 4.6e-02 | 1.0 / 6.2e-02 | 0.8 / 5.2e-02 | 1.6 / 0.1 | 1.0 / 6.2e-02 | 5.5 / 0.4 | 0.7 / 4.5e-02 | 0.8 / 4.9e-02 | 8.4 / 0.5 | 0.9 / 6.0e-02 |
| F | 10.2 / 0.7 | 0.9 / 5.6e-02 | 0.7 / 5.1e-02 | 1.6 / 0.1 | 0.9 / 5.8e-02 | 1.8 / 0.1 | 0.8 / 4.9e-02 | 0.8 / 5.5e-02 | 0.9 / 6.2e-02 | 9.6 / 0.6 | 2.1 / 0.1 | 1.0 / 6.3e-02 |
| G | 1.2 / 7.7e-02 | 0.8 / 5.2e-02 | 0.7 / 4.8e-02 | 0.8 / 5.3e-02 | 10.1 / 0.7 | 0.9 / 6.1e-02 | 0.9 / 5.5e-02 | 0.7 / 4.3e-02 | 0.8 / 5.0e-02 | 0.8 / 5.4e-02 | 0.7 / 4.5e-02 | 5.5 / 0.4 |
| H | 1.2 / 8.0e-02 | 1.5 / 9.9e-02 | 8.0 / 0.5 | 0.7 / 4.7e-02 | 0.9 / 0.6 | 0.9 / 5.7e-02 | 0.8 / 5.1e-02 | 0.8 / 5.2e-02 | 9.7 / 0.6 | 0.9 / 5.8e-02 | 1.0 / 6.3e-02 | 9.3 / 0.6 |

*FIG. 11B*

|   | 1 | 2 | 3 | 4 | 5 | 6 | 7 | 8 | 9 | 10 | 11 | 12 |
|---|---|---|---|---|---|---|---|---|---|---|---|---|
| A | 1.0 / 4.8e-02 | 1.0 / 5.1e-02 | 3.3 / 0.2 | 5.5 / 0.3 | 2.1 / 0.1 | 3.1 / 0.2 | 5.1 / 0.3 | 3.5 / 0.2 | 4.0 / 0.2 | 3.1 / 0.2 | 2.8 / 0.1 | 3.4 / 0.2 |
| B | 2.0 / 0.1 | 1.0 / 4.8e-02 | 3.4 / 0.2 | 3.0 / 0.1 | 3.2 / 0.2 | 2.9 / 0.1 | 2.9 / 0.1 | 2.8 / 0.1 | 1.1 / 5.5e-02 | 2.8 / 0.1 | 2.5 / 0.1 | 3.1 / 0.2 |
| C | 1.1 / 5.4e-02 | 3.4 / 0.2 | 5.2 / 0.3 | 3.2 / 0.2 | 4.4 / 0.2 | 2.3 / 0.1 | 6.0 / 0.3 | 1.6 / 8.0e-02 | 1.1 / 5.2e-02 | 2.8 / 0.1 | 2.7 / 0.1 | 1.0 / 5.1e-02 |
| D | 1.3 / 6.7e-02 | 1.0 / 4.8e-02 | 5.0 / 0.2 | 3.2 / 0.2 / 1.2 / 5.7e-02 | 3.6 / 0.2 | 2.6 / 0.1 | 2.4 / 0.1 | 3.2 / 0.2 | 1.2 / 5.9e-02 | 2.4 / 0.1 | 2.6 / 0.1 | 2.9 / 0.1 |
| E | 1.0 / 5.0e-02 | 3.0 / 0.1 | 2.8 / 0.1 | 4.6 / 0.2 | 1.1 / 5.3e-02 | 2.9 / 0.1 | 2.5 / 0.1 | 1.2 / 5.8e-02 | 1.6 / 7.7e-02 | 2.9 / 0.1 | 2.1 / 0.1 | 2.4 / 0.1 |
| F | 1.9 / 9.4e-02 | 1.1 / 5.5e-02 | 2.5 / 0.1 | 2.6 / 0.1 | 2.8 / 0.1 | 1.4 / 7.1e-02 | 2.2 / 0.1 | 1.4 / 7.1e-02 | 2.4 / 0.1 | 1.1 / 5.4e-02 | 1.0 / 5.1e-02 | 2.4 / 0.1 |
| G | 3.0 / 0.1 | 3.1 / 0.2 | 1.2 / 5.9e-02 | 1.3 / 6.6e-02 | 2.7 / 0.1 | 2.3 / 0.1 | 2.5 / 0.1 | 1.6 / 8.1e-02 | 3.2 / 0.2 | 1.0 / 5.1e-02 | 2.3 / 0.1 | 1.3 / 6.2e-02 |
| H | 2.3 / 0.1 | 2.5 / 0.1 | 1.2 / 5.9e-02 | 2.1 / 0.1 | 2.4 / 0.1 | 3.7 / 0.2 | 2.6 / 0.1 | 1.6 / 7.7e-02 | 2.4 / 0.1 | 1.5 / 7.4e-02 | 4.1 / 0.2 | 8.3 / 0.4 |

| | 1 | 2 | 3 | 4 | 5 | 6 | 7 | 8 | 9 | 10 | 11 | 12 |
|---|---|---|---|---|---|---|---|---|---|---|---|---|
| A | 1.0 / 5.2e-02 | 1.0 / 5.0e-02 | 2.6 / 0.1 | 8.3 / 0.4 | 1.8 / 9.4e-02 | 8.4 / 0.4 | 8.5 / 0.4 | 1.2 / 6.0e-02 | 1.1 / 5.5e-02 | 2.0 / 0.1 | 1.2 / 6.0e-02 | 14.3 / 0.7 |
| B | 5.1 / 0.3 | 1.1 / 5.5e-02 | 10.0 / 0.5 | 8.2 / 0.4 | 7.4 / 0.4 | 1.4 / 7.1e-02 | 7.5 / 0.4 | 7.8 / 0.4 | 9.3 / 0.5 | 8.0 / 0.4 | 4.2 / 0.2 | 2.0 / 0.1 |
| C | 1.3 / 6.7e-02 | 8.4 / 0.4 | 7.9 / 0.4 | 2.2 / 0.1 | 9.6 / 0.5 | 7.5 / 0.4 | 6.6 / 0.3 | 7.1 / 0.4 | 9.8 / 0.5 | 7.5 / 0.4 | 8.2 / 0.4 | 5.5 / 0.3 |
| D | 1.4 / 7.3e-02 | 2.0 / 0.1 | 4.1 / 0.2 | 8.8 / 0.4 | 7.4 / 0.4 | 7.1 / 0.4 | 4.7 / 0.2 | 8.6 / 0.4 | 4.1 / 0.2 | 7.5 / 0.4 | 1.4 / 7.0e-02 | 8.4 / 0.4 |
| E | 1.1 / 5.4e-02 | 7.5 / 0.4 | 7.4 / 0.4 | 3.5 / 0.2 | 8.5 / 0.4 | 2.8 / 0.1 | 7.0 / 0.4 | 1.3 / 6.4e-02 | 7.5 / 0.4 | 3.2 / 0.2 | 1.0 / 5.1e-02 | 8.2 / 0.4 |
| F | 7.6 / 0.4 | 8.1 / 0.4 | 8.3 / 0.4 | 7.1 / 0.4 | 6.5 / 0.3 | 3.1 / 0.2 | 7.0 / 0.4 | 1.1 / 5.4e-02 | 5.1 / 0.3 | 1.0 / 5.1e-02 | 7.7 / 0.4 | 8.6 / 0.4 |
| G | 10.9 / 0.6 | 8.2 / 0.4 | 7.4 / 0.4 | 8.0 / 0.4 | 7.4 / 0.4 | 8.7 / 0.4 | 10.0 / 0.5 | 7.2 / 0.4 | 1.7 / 8.8e-02 | 8.1 / 0.4 | 7.4 / 0.4 | 1.4 / 7.1e-02 |
| H | 2.2 / 0.1 | 1.3 / 6.8e-02 | 2.2 / 0.1 | 11.2 / 0.6 | 1.7 / 8.6e-02 | 9.3 / 0.5 | 9.1 / 0.5 | 5.4 / 0.3 | 0.9 / 4.4e-02 | 7.9 / 0.4 | 1.6 / 8.3e-02 | 12.5 / 0.6 |

FIG. 13

|  |  | 39 | *AFKNDDQKS | AYALGASLGR | YMENSLKEQE | KLGIKLDKDQ | LIAGVQDAFA 87 |
|---|---|---|---|---|---|---|---|
| N-term.E.coliO6 FkpA(SwisProt P65764) | | | | | | | |
| Enterobacter clocae | (CBK86063) | | ---------- | ---------- | ---------- | --V----N- | ---------- |
| Cronobacter sakazakii | (YP_001440409) | | --Q------- | ---------- | ---------- | ---------- | ---------- |
| Klebsialla pneumoniae | (YP_002921574) | | ---------- | ---------- | ---------- | -----S---- | ---------- |
| Citrobacter koseri | (YP_001456234) | | ---------- | ---------- | ---------- | ---------- | ---------- |
| Escherichia coli K-12 | (NP_417806) | | ---------- | ---------- | ---------- | ---------- | ---------- |
| Shigella flexneri | (NP_709121) | | S--------- | ---------- | ---------- | ---------- | ---------- |
| Shigella boydii | (YP_001882020) | | ---------- | ---------- | ---------- | ---------- | ---------- |
| Shigella dysenteria | (YP_404977) | | ---------- | ---------- | ---------- | ---------- | ---------- |
| Escherichia albertii | (ZP_02904021) | | E--------- | ---------- | ---------- | ---------- | ---------- |
| Escherichia fergusonii | (YP_002384399) | | --A------- | ---------- | -------Q-- | ---------- | ---------- |
| Citrobacter rodentium | (YP_003367879) | | ---------- | ---------- | ---------- | ---------- | ---------- |
| Yersinia kristensenii | (ZP_04624699) | | -----Q---- | ---------- | ------D--- | -----N---- | ---------- |
| Serratia odorifera | (ZP_06637638) | | K----EQA-- | ---------- | ------D--- | ---------- | ---------- |

|  |  | 88 | *DKSKLSDQEI | EQTLQAFEAR | VKSSAQAKME | KDAADNEAKG | KEYREKFAKEK 138 |
|---|---|---|---|---|---|---|---|
| N-term.E.coliO6 FkpA(SwisProt P65764) | | | | | | | |
| Enterobacter clocae | (CBK86063) | | ---------- | ---------- | -GA--T---- | A--K------ | -A--D------ |
| Cronobacter sakazakii | (YP_001440409) | | ---------- | -------T-- | -GA------V | ---TE----- | -AF-D------ |
| Klebsialla pneumoniae | (YP_002921574) | | ---------- | ---------- | ---TA--Q-- | ---TE----- | -AF-DN----- |
| Citrobacter koseri | (YP_001456234) | | ---------- | -------T-- | ----T----- | ---------- | -AF-------- |
| Escherichia coli K-12 | (NP_417806) | | ---------- | ---------- | ---------- | ---------- | ----------- |
| Shigella flexneri | (NP_709121) | | ---------- | ---------- | ---------- | ---------- | ----------- |
| Shigella boydii | (YP_001882020) | | --N------- | ---------- | ---------- | ---------- | ----------- |
| Shigella dysenteria | (YP_404977) | | ---------- | ---------- | ---------- | ---------- | ----------- |
| Escherichia albertii | (ZP_02904021) | | ---------- | ---------- | ---A------ | ----E----- | ----D------ |
| Escherichia fergusonii | (YP_002384399) | | Q--------- | ---T------ | ---TA----- | ---------- | ----------- |
| Citrobacter rodentium | (YP_003367879) | | ---T-E---- | --K---G--- | ---A------ | ----E----- | ----D------ |
| Yersinia kristensenii | (ZP_04624699) | | S---T-E--- | --K---G--- | ---A----R- | Q--KE-AD-- | -AK---T---- |
| Serratia odorifera | (ZP_06637638) | | N----N-AD- | ---------- | ---------- | Q--K------ | -AK--DT---- |

```
                              139                                                               187
                                *                                                **
C-term.E.coliO6 FkpA(SwisProt P65764) *GVKTSSTGL VYQVVEAGKG EAPKDSDTVV VNYKGTLIDG KEFDNSYTRG
Salmonella enterica    (NP_462357)     ---------  L-K-EKE-T- ---------- ---------- ----------
Citrobacter koseri     (YP_001456234)  -A-------  --K-EK---T- ---------- ---------- ----------
Klebsialla pneumonia   (YP_001337386)  -----K---  L-K-EKE-A- D--------- ---------- ----------
Enterobacter cloacae   (YP_003939943)  ---------  L-K-EKE-T- D--------- ---------- ----------
Cronobacter sakazakii  (YP_001440409)  ---------  L-K-EKE-T- A-------E- -------Q-- -------K--
Erwinia tasmaniensis   (YP_001909086)  ---KTES--  L----AKE-T- -V-------I ---------- ----------
Erwinia billingiae     (YP_003743520)  ---KTES--  L---EKE-T- D--------- ---------T ----------
Edwardsiella tarda     (YP_003297282)  ----TAS--  M-L-QKE-T- P--T------ ------S-N- -------T--S-
Sodalis glossinidius   (YP_455971)     --KTAN-V   L-K-DK---T- N--T------ ---------V ----------T-K--
Yersinia kristensenii  (ZP_04624699)   D--KTES--  L-K-EK---T- ---------- -------T-- ----------T-K--
Serratia odorifera     (ZP_06192651)   ---KTES--  L-K-EKP-A- ---------- -------T-- -------T--
Citrobacter rodentium  (YP_003367879)  D--------  L-K-EK---T- ---------- ---------- ----------
Escherichia fergusonii (YP_002384399)  D--------  --K-EK---T- ---------- ---------- ----------
Escherichia albertii   (ZP_02904021)   ---------  ---EK----- ---------- ---------- ----------
Shigella dysenteriae   (YP_404977)     ---------  ---------- ---------- ---------- -------I--
Shigella flexneri      (NP_709121)     ---------  ---------- ---------- ---------- ----------
Escherichia coli K-12  (NP_417806)     ---------  ---------- ---------- ---------- ----------
```

FIG. 13 (Cont.)

| | 188 | | | | | | | 248 |
|---|---|---|---|---|---|---|---|---|
| C-term.E.coli06 FkpA(SwisProt P65764) | *EPLSFRLDGV | IPGWTEGLKN | IKKGGKIKLV | IPPELAYGKA | GVPGIPPNST | LVFDVELLDVK | | |
| Salmonella enteric (NP_462357) | ---------- | ---------- | ---------- | -------T-- | -------A-- | -I--------- | | |
| Citrobacter koseri (YP_001456234) | ---------- | ---------- | -------QM- | ---D----T- | ---------- | -I--------- | | |
| Klebsialla pneumonia (YP_001337386) | ---------- | ---------- | ---------- | ---D----T- | -------A-- | -I--------- | | |
| Enterobacter cloacae (YP_003939943) | ---------- | ---------- | ------V--- | ---D----T- | -------A-- | -I--------- | | |
| Cronobacter sakazakii (YP_001440409) | ---------- | ---------- | ------V-M- | ---D----T- | -------A-- | -I--------- | | |
| Erwinia tasmaniensis (YP_001909086) | ---------- | -----H--V- | ---------- | --N-----N- | -------V-- | -I--------- | | |
| Erwinia billingiae (YP_003743520) | ---------- | -----H--V- | ---------- | --Q-----N- | -------A-- | -I--------- | | |
| Edwardsiella tarda (YP_003297282) | ---------- | -----H---- | ---------- | ---D----T- | -------A-- | ------E---- | | |
| Sodalis glossinidius (YP_455971) | ---------- | -----H---- | -------Q-- | --Q-----T- | S------A-- | -I--------- | | |
| Yersinia kristensenii (ZP_04624699) | ---------- | ---------- | ------VT-- | ---------- | -------A-- | -I--------- | | |
| Serratia odorifera (ZP_06192651) | ---------- | -----H--L- | ---------- | --A-----T- | -------A-- | -I--------- | | |
| Citrobacter rodentium (YP_003367879) | ---------- | ---------- | ---------- | ---D----T- | -------A-- | -I--------- | | |
| Escherichia fergusonii (YP_002384399) | -----Q---- | -------Y-- | ---------- | ---T----N- | ---------- | ----------- | | |
| Escherichia albertii (ZP_02904021) | ---------- | ---------- | ---------- | ---------- | ---------- | ----------- | | |
| Shigella dysenteriae (YP_404977) | ---------- | ---------- | ---------- | ---------- | ---------- | ----------- | | |
| Shigella flexneri (NP_709121) | ---------- | ---------- | ---------- | ---------- | ---------- | ----------- | | |
| Escherichia coli K-12 (NP_417806) | ---------- | ---------- | ---------- | ---------- | ---------- | ----------- | | |

*Residues 39-248 of SEQ ID NO: 1
** Boxed region corresponds to peptidyl-prolyl isomerase domain

★ = stop codon(s)
HMV=Triple (6His-cmyc-V5) tag

| LANE | 1 | 2 | 3 | 4 |
|---|---|---|---|---|
| SAMPLE | TG1 | TG1 | FkpA (-) | FkpA (-) |
| EXTRACT | IN PERIPLASM | IN CYTOPLASM | IN PERIPLASM | IN CYTOPLASM |

FIG. 18A
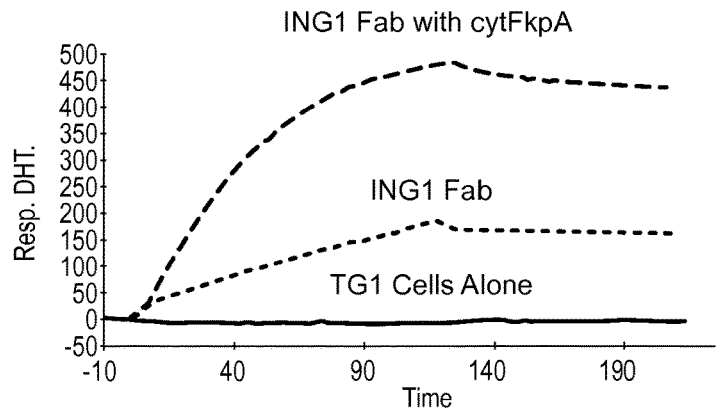
FIG. 18B
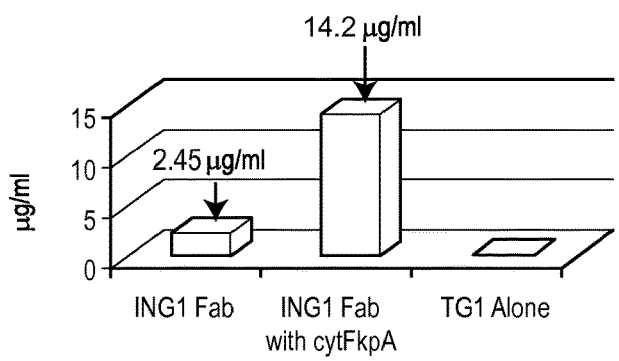
FIG. 18C
| SAMPLE (PPE) | Total ING1 F$_{AB}$ (μg/ml) | F$_{AB}$ Capture (RU) | Ligand Bound (RU) | Specific Activity (%) | Active FAB (μg/ml) |
|---|---|---|---|---|---|
| ING1 | 2.45 | 162.5 | 17.2 | 13.2 | 0.3 |
| ING1+cytFkpA | 14.20 | 187.4 | 19.7 | 13.1 | 1.9 |

SEQUENCE LISTING

<160> NUMBER OF SEQ ID NOS: 4

<210> SEQ ID NO 1
<211> LENGTH: 270
<212> TYPE: PRT
<213> ORGANISM: Escherichia coli

<400> SEQUENCE: 1

```
Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
            20                  25                  30

Thr Thr Ala Asp Ser Lys Ala Ala Phe Lys Asn Asp Asp Gln Lys Ser
        35                  40                  45

Ala Tyr Ala Leu Gly Ala Ser Leu Gly Arg Tyr Met Glu Asn Ser Leu
    50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
    130                 135                 140

Ser Thr Gly Leu Val Tyr Gln Val Val Glu Ala Gly Lys Gly Glu Ala
145                 150                 155                 160

Pro Lys Asp Ser Asp Thr Val Val Asn Tyr Lys Gly Thr Leu Ile
                165                 170                 175

Asp Gly Lys Glu Phe Asp Asn Ser Tyr Thr Arg Gly Glu Pro Leu Ser
                180                 185                 190

Phe Arg Leu Asp Gly Val Ile Pro Gly Trp Thr Glu Gly Leu Lys Asn
            195                 200                 205

Ile Lys Lys Gly Gly Lys Ile Lys Leu Val Ile Pro Pro Glu Leu Ala
        210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270
```

```
<210> SEQ ID NO 2
<211> LENGTH: 161
<212> TYPE: PRT
<213> ORGANISM: Escherichia coli

<400> SEQUENCE: 2

Met Lys Lys Trp Leu Leu Ala Ala Gly Leu Gly Leu Ala Leu Ala Thr
1               5                   10                  15

Ser Ala Gln Ala Ala Asp Lys Ile Ala Ile Val Asn Met Gly Ser Leu
            20                  25                  30

Phe Gln Gln Val Ala Gln Lys Thr Gly Val Ser Asn Thr Leu Glu Asn
        35                  40                  45

Glu Phe Lys Gly Arg Ala Ser Glu Leu Gln Arg Met Glu Thr Asp Leu
    50                  55                  60

Gln Ala Lys Met Lys Lys Leu Gln Ser Met Lys Ala Gly Ser Asp Arg
65                  70                  75                  80

Thr Lys Leu Glu Lys Asp Val Met Ala Gln Arg Gln Thr Phe Ala Gln
                85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys

<210> SEQ ID NO 3
<211> LENGTH: 245
<212> TYPE: PRT
<213> ORGANISM: Escherichia coli

<400> SEQUENCE: 3

Ile Glu Ala Ala Lys Pro Ala Thr Thr Ala Asp Ser Lys Ala Ala Phe
1               5                   10                  15

Lys Asn Asp Asp Gln Lys Ser Ala Tyr Ala Leu Gly Ala Ser Leu Gly
            20                  25                  30

Arg Tyr Met Glu Asn Ser Leu Lys Glu Gln Glu Lys Leu Gly Ile Lys
        35                  40                  45

Leu Asp Lys Asp Gln Leu Ile Ala Gly Val Gln Asp Ala Phe Ala Asp
    50                  55                  60

Lys Ser Lys Leu Ser Asp Gln Glu Ile Glu Gln Thr Leu Gln Ala Phe
65                  70                  75                  80

Glu Ala Arg Val Lys Ser Ser Ala Gln Ala Lys Met Glu Lys Asp Ala
                85                  90                  95

Ala Asp Asn Glu Ala Lys Gly Lys Glu Tyr Arg Glu Lys Phe Ala Lys
            100                 105                 110

Glu Lys Gly Val Lys Thr Ser Ser Thr Gly Leu Val Tyr Gln Val Val
        115                 120                 125

Glu Ala Gly Lys Gly Glu Ala Pro Lys Asp Ser Asp Thr Val Val Val
    130                 135                 140

Asn Tyr Lys Gly Thr Leu Ile Asp Gly Lys Glu Phe Asp Asn Ser Tyr
145                 150                 155                 160

Thr Arg Gly Glu Pro Leu Ser Phe Arg Leu Asp Gly Val Ile Pro Gly
                165                 170                 175
```

```
Trp Thr Glu Gly Leu Lys Asn Ile Lys Lys Gly Gly Lys Ile Lys Leu
            180                 185                 190

Val Ile Pro Pro Glu Leu Ala Tyr Gly Lys Ala Gly Val Pro Gly Ile
        195                 200                 205

Pro Pro Asn Ser Thr Leu Val Phe Asp Val Glu Leu Leu Asp Val Lys
    210                 215                 220

Pro Ala Pro Lys Ala Asp Ala Lys Pro Glu Ala Asp Ala Lys Ala Ala
225                 230                 235                 240

Asp Ser Ala Lys Lys
                245

<210> SEQ ID NO 4
<211> LENGTH: 141
<212> TYPE: PRT
<213> ORGANISM: Escherichia coli

<400> SEQUENCE: 4

Ala Asp Lys Ile Ala Ile Val Asn Met Gly Ser Leu Phe Gln Gln Val
1               5                   10                  15

Ala Gln Lys Thr Gly Val Ser Asn Thr Leu Glu Asn Glu Phe Lys Gly
            20                  25                  30

Arg Ala Ser Glu Leu Gln Arg Met Glu Thr Asp Leu Gln Ala Lys Met
        35                  40                  45

Lys Lys Leu Gln Ser Met Lys Ala Gly Ser Asp Arg Thr Lys Leu Glu
    50                  55                  60

Lys Asp Val Met Ala Gln Arg Gln Thr Phe Ala Gln Lys Ala Gln Ala
65                  70                  75                  80

Phe Glu Gln Asp Arg Ala Arg Arg Ser Asn Glu Glu Arg Gly Lys Leu
                85                  90                  95

Val Thr Arg Ile Gln Thr Ala Val Lys Ser Val Ala Asn Ser Gln Asp
            100                 105                 110

Ile Asp Leu Val Val Asp Ala Asn Ala Val Ala Tyr Asn Ser Ser Asp
        115                 120                 125

Val Lys Asp Ile Thr Ala Asp Val Leu Lys Gln Val Lys
    130                 135                 140
```

METHODS AND MATERIALS FOR ENHANCING FUNCTIONAL PROTEIN EXPRESSION IN BACTERIA

CROSS REFERENCE TO RELATED APPLICATIONS

This application claims priority to U.S. Provisional Application No. 61/439,232, filed Feb. 3, 2011, incorporated by reference in its entirety.

INCORPORATION BY REFERENCE OF MATERIAL SUBMITTED ELECTRONICALLY

Incorporated by reference in its entirety is a computer-readable amino acid sequence listing submitted concurrently herewith and identified as follows: One 8,192 byte ASCII (Text) file named "45785A_seq_listing.txt" created on Feb. 3, 2012.

FIELD OF THE INVENTION

The invention relates to materials and methods useful for expressing heterologous proteins in prokaryotic cells.

BACKGROUND

FkpA is a periplasmic protein of *E. coli* exhibiting both molecular chaperone and cis-trans peptidyl-prolyl isomerase activities. Native FkpA is localized to the periplasmic space as a 245 amino acid homodimer in *E. coli* by virtue of a signal sequence directing secretion to the periplasm. The chaperone activity of FkpA resides in the first 120 amino acids of the mature protein and the peptidyl-prolyl isomerase activity resides in amino acids 121 to 245. The effect of FkpA overexpression in the periplasm on periplasmic yields of antibody single chain variable fragments (scFvs) has been studied. See Ramm and Pluckthun, *J Biol Chem,* 275:22, 17106-17113 (2000).

Skp is a 17-kDa periplasmic chaperone for outer membrane protein assembly in *E. coli* that facilitates proper folding of outer membrane protein intermediates and helps to maintain their solubility. Skp functions as a homotrimer and belongs to a family of cavity-containing chaperones that bind their substrates in the cavity, thereby providing a suitable environment for proper folding and protecting the substrate from aggregation. The effect of co-expression of Skp in the cytoplasm and a Fab antibody fragment in the bacterial cytoplasm has been studied. See Levy et al., *Protein Expr Purif.* 23(2):338-47 (2001).

A common problem with expressing heterologous proteins, such as antibodies, in prokaryotic systems is aggregation of the heterologous protein to such an extent that a significant portion of the protein is insoluble or nonfunctional. The methods and materials of the invention provide a solution to this problem.

SUMMARY OF THE INVENTION

This disclosure relates to methods and materials useful for improving the yield of heterologously expressed proteins (e.g., antibodies) in prokaryotic cells (e.g., *E. coli* cells). Prokaryotic host cells are provided that express FkpA and/or Skp in the cytoplasm and secrete heterologous proteins-of-interest (e.g., antibodies). The inventors have unexpectedly discovered that *E. coli* cells expressing FkpA and Skp lacking signal sequences, such that FkpA and Skp are localized to the cytoplasm rather than the periplasm, significantly improve the yield of secreted, soluble, correctly folded and functional heterologous proteins in the *E. coli* periplasm.

One aspect of the disclosure provides a prokaryotic host cell that expresses a heterologous protein for recombinant production comprising (a) a polynucleotide encoding (i) FkpA that is not linked to a functional signal sequence, or a functional fragment thereof, or (ii) Skp that is not linked to a functional signal sequence, or a functional fragment thereof, and (b) a polynucleotide encoding this heterologous protein, wherein the heterologous protein is linked to a functional signal sequence. In some embodiments, the host cell comprises both (i) a polynucleotide encoding FkpA that is not linked to a functional signal sequence, or a functional fragment thereof, and (ii) a polynucleotide encoding Skp that is not linked to a functional signal sequence, or a functional fragment thereof. In some embodiments, the polynucleotides are in the same vector; and in other embodiments they are in different vectors. In some embodiments the two polynucleotides are expressed on the same messenger RNA.

Related aspects of the disclosure provide these polynucleotides operably linked to regulatory control sequences, which act to regulate expression of the encoded protein(s). Another related aspect provides vectors or chromosomes comprising these polynucleotides. A further related aspect of the disclosure provides host cells comprising such polynucleotides and/or vectors and/or chromosomes, and methods of using such host cells to express recombinantly such heterologous proteins, including antibodies and antibody fragments. Yet another related aspect of the disclosure provides the heterologous proteins encoded by the polynucleotides, either displayed on the surface of a phage particle, or in an isolated or purified form.

In some or any of the embodiments described herein, the prokaryotic host cell is selected from the group consisting of *Escherichia coli, Salmonella typhimurium, Bacillus subtilis, Pseudomonas aeruginosa,* and *Serratia marcescans.* In example embodiments, the prokaryotic host cell is *E. coli.*

In some or any of the embodiments described herein, the heterologous protein is associated with mis-folding or a slow folding rate in the absence of FkpA and Skp. Such heterologous proteins include: growth factors (e.g. epidermal growth factor, insulin-like growth factor-1); blood clotting factors (e.g. anti-hemophilic factor); hormones (e.g., insulin, glucagon, growth hormone, somatotropin, erythropoietin); cytokines (e.g., interferons, interleukins; granuloctye colony-stimulating factor, granulocyte-macrophage colony-stimulating factor, CD86); chemokines (e.g., CCL3); receptors (e.g., chemokine receptors, tyrosine kinase receptors); enzymes (e.g., proteases, lipases, carbohydrases, chymosin, DNAase, prourokinase, arginine deaminase, cytosine deaminase, L-asparaginase); enzyme activators (e.g., tissue-type plasminogen activator); enzyme inhibitors (e.g, tissue inhibitors of metalloproteases); peptides (e.g., hirudin, neuregulin-1 fragments); antibody fragments (e.g., Fab fragments); protein scaffolds (e.g. Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-1β-lactamase, fibronectin type III domains, CTLA-4, T-cell resptors, knottins, neocarzinostatin, carbohydrate binding module 4-2, green fluorescent protein, thioredoxin); vaccines (e.g. influenza vaccines, anthrax vaccines such as rPA vaccines, hepatitis E virus vaccines such as ORF2 vaccines, human papilloma virus vaccines); toxins; and immunotoxins (Misawa and Kumagai, *Biopolymers* 51: 297-307 (1999); Zhang et al, *Protein Expr. Purif.* 25(1):105-13 (2002); Demain, *Trends in Biotech.* 18(1): 26-31 (2000); Gebauer & Skerra, *Curr. Opin. Chem. Biol.* 13:245-55 (2009); Gill & Damle, *Curr. Opin. Biotech* 17: 653-58 (2006); Hosse et al, Protein Sci. 15:14-27 (2006); Skerra, *Curr. Opin. Biotech* 18: 295-3-4 (2007); Song et al, *PLoS ONE* 3(5): e2257 (2008); Vahedi et al, *Applied Biochem. and Biotech.* 157(3): 554-61 (2009); Hakim and Benhar, *MAbs.* 1(3): 281-87 (2009)).

In some or any of the embodiments described herein, the heterologous protein is proline isomerization-dependent. In example embodiments, the proline isomerization-dependent heterologous protein is an antibody or antibody fragment comprising a kappa light chain.

In some or any of the embodiments herein, the heterologous protein is fused to a filamentous phage coat protein or fragment thereof. In example embodiments, the host cells comprising heterologous proteins fused to a filamentous phage coat protein or fragment thereof are used to produce phage particles displaying the heterologous proteins on their surfaces.

In some or any of the embodiments described herein, the heterologous protein is an antibody. In example embodiments, the antibody is an antibody fragment selected from the group consisting of an Fv, a disulfide-linked Fv, an scFv, a kappa light chain fragment, a lambda light chain fragment, and a Fab fragment.

In some or any of the embodiments herein, the functional fragment of FkpA comprises a chaperone domain fragment, for example, amino acids 26-140 of SEQ ID NO: 1 or a fragment or variant thereof that retains the ability to increase yield of functional heterologous protein. In example embodiments, the chaperone domain fragment comprises an amino acid sequence at least 75% identical to at least 100 amino acids of amino acids 26 through 140 of SEQ ID NO: 1.

In some or any of the embodiments herein, the functional fragment of FkpA comprises a peptidylprolyl isomerase domain fragment, for example, amino acids 141-270 of SEQ ID NO: 1 or a fragment or variant thereof that retains the ability to increase yield of functional heterologous protein. In example embodiments, the peptidylprolyl isomerase domain fragment comprises an amino acid sequence at least 75% identical to a fragment of at least 100 amino acids of amino acids 141 through 270 of SEQ ID NO: 1.

In some or any of the embodiments herein, the functional fragment of Skp comprises amino acids 21-161 of SEQ ID NO: 2 or a fragment or variant thereof that retains the ability to increase yield of functional heterologous protein. In example embodiments, the functional fragment of Skp comprises an amino acid sequence at least 75% identical to a fragment of at least 100 amino acids of SEQ ID NO: 2.

In some or any of the embodiments described herein, there is provided a plurality of cells comprising at least about $10^3$, $10^4$, $10^5$, $10^6$, $10^7$, $10^8$, $10^9$, or more, different prokaryotic host cells according to any of the embodiments described herein, each such host cell expressing a different heterologous protein (e.g., an antibody, such as a single chain antibody).

Another aspect of the disclosure provides a method for increasing recombinant production of a functional heterologous protein (e.g., an antibody) in a prokaryotic host cell, comprising co-expressing a polynucleotide selected from the group consisting of a polynucleotide encoding FkpA that is not linked to a functional signal sequence, or a functional fragment thereof, and a polynucleotide encoding Skp that is not linked to a functional signal sequence, or a functional fragment thereof; and a polynucleotide encoding a heterologous protein linked to a functional signal sequence, whereby the amount of functional heterologous protein produced is increased compared to expressing the heterologous protein in the absence of FkpA and/or Skp.

In some or any of the embodiments herein, the signal sequence linked to the heterologous protein directs secretion of the heterologous protein to the periplasm.

The polynucleotides of the disclosure may be operably linked to regulatory control sequences, such as promoters, enhancers or one or more other transcriptional regulatory sequences, optionally as part of a vector comprising these sequences. In some or any embodiments, the polynucleotide encoding (a) (i) FkpA that is not linked to a functional signal sequence, or a functional fragment thereof, or (ii) Skp that is not linked to a functional signal sequence, or a functional fragment thereof, and (b) the polynucleotide encoding the heterologous protein linked to a functional signal sequence, are operatively linked to the same regulatory sequence (i.e., the coding sequences are polycistronic). Host cells comprising such polynucleotides or vectors may be prepared using methods known in the art or described herein.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment," "some embodiments," "further embodiment," "specific exemplary embodiments," and/or "another embodiment," each of these types of embodiments is a non-limiting example of a feature that is intended to be combined with any other feature, or combination of features, described herein without having to list every possible combination. Such features or combinations of features apply to any of the aspects of the invention. Similarly, where the disclosure describes polynucleotides encoding polypeptides characterized by certain features, polypeptides characterized by those features, host cells expressing such polypeptides, and all related methods of using such host cells are also contemplated by the disclosure. Where examples of values falling within ranges are disclosed, any of these examples are contemplated as possible endpoints of a range, any and all numeric values between such endpoints are contemplated, and any and all combinations of upper and lower endpoints are envisioned.

Numerous additional aspects and advantages of the invention will become apparent to those skilled in the art upon consideration of the following detailed description of the invention which describes presently preferred embodiments thereof. All U.S. patents, U.S. patent application publications, U.S. patent applications, foreign patents, foreign patent applications, and non-patent publications referred to in this application, are incorporated herein by reference, in their entireties.

BRIEF DESCRIPTION OF THE DRAWINGS

FIG. 5 illustrates the results of an ELISA to detect the total amount of the murine light kappa anti-human insulin receptor 83-7 Fab or the functional 83-7 Fab expressed in *E. coli* strains expressing various combinations of FkpA and Skp constructs. FIG. 5A is an antibody dilution series detecting the total amount of 83-7 Fab produced while

FIG. 6 illustrates the results of an ELISA to detect the total amount of the human kappa BM7-2 Fab (which recognizes a proprietary kinase) or the functional BM7-2 Fab expressed in *E. coli* strains expressing cytoplasmic FkpA (light grey bars) or both cytoplasmic FkpA and cytoplasmic Skp (dark grey bars) constructs. FIG. 6A is an antibody dilution series detecting the total amount of BM7-2 Fab produced while

FIG. 8 illustrates the results of an ELISA to detect the total and functional human lambda light chain of A10, C10, D1, and E6 Fabs expressed in *E. coli* strains expressing cytoplasmic FkpA or both cytoplasmic FkpA and cytoplasmic Skp constructs. FIG. 8A is an antibody dilution series detecting the total amount of the indicated Fab produced while

FIG. 10 illustrates the results of a phage panning assay to detect kappa light chain Fabs with the ability to bind a target antigen. FIG. 10A displays the results of an ELISA to detect Fabs from the phage display library without expression of cytoplasmic FkpA while 10B displays the results of an ELISA to detect Fabs from the library with expression of cytoplasmic FkpA. Positive clones identified in the assay are shown in bold.

FIG. 11 illustrates the results of a phage panning assay to detect lambda light chain Fabs with the ability to bind a target antigen. FIG. 11A displays the results of an ELISA to detect Fabs from the phage display library without expression of cytoplasmic FkpA while 11B displays the results of an ELISA to detect Fabs from the library with expression of cytoplasmic FkpA. Positive clones identified in the assay are shown in bold.

FIG. 12 illustrates the results of a phage panning assay to detect scFvs with the ability to bind a target antigen. FIG. 12A displays the results of an ELISA to detect scFvs from the phage display library without expression of cytoplasmic FkpA while 12B displays the results of an ELISA to detect scFvs from the library with expression of cytoplasmic FkpA. Positive clones identified in the assay are shown in bold.

FIG. 13 depicts amino acid sequence alignments of FkpA orthologs from a variety of bacterial species with residues 39-248 of FkpA from *E. coli* 06 (residues 39-248 of SEQ ID NO: 1).

FIG. 14 illustrates the results of a phage panning assay to detect lambda Fabs and kappa Fabs with the ability to bind TIE2. The absorbance at 450 nm after development of the ELISA is the lower number in each square and the upper number is the fold-over background negative controls (A1 and A2). Positive clones identified in the assay are shown in bold. Well H12 is a positive control. The circles represent clones with unique amino acid sequences.

FIGS. 18A and 18B illustrate SPR sensograms (FIG. 18A) and a chart (FIG. 18B) of the estimated periplasmic ING1 Fab yields based on a standard curve. The total yield of ING1 Fab (14.2 µg/ml) was dramatically increased upon coexpression of cytFkpA in the *E. coli* cytoplasm. FIG. 18C illustrates the amount of active ING1 Fab bound to the antigen EpCAM and its specific activity, calculated as described in Example 1. Coexpression of cytFkpA increased the amount of functional ING1 Fab. Its specific activity remained unchanged.

DETAILED DESCRIPTION OF THE INVENTION

Figure 1:
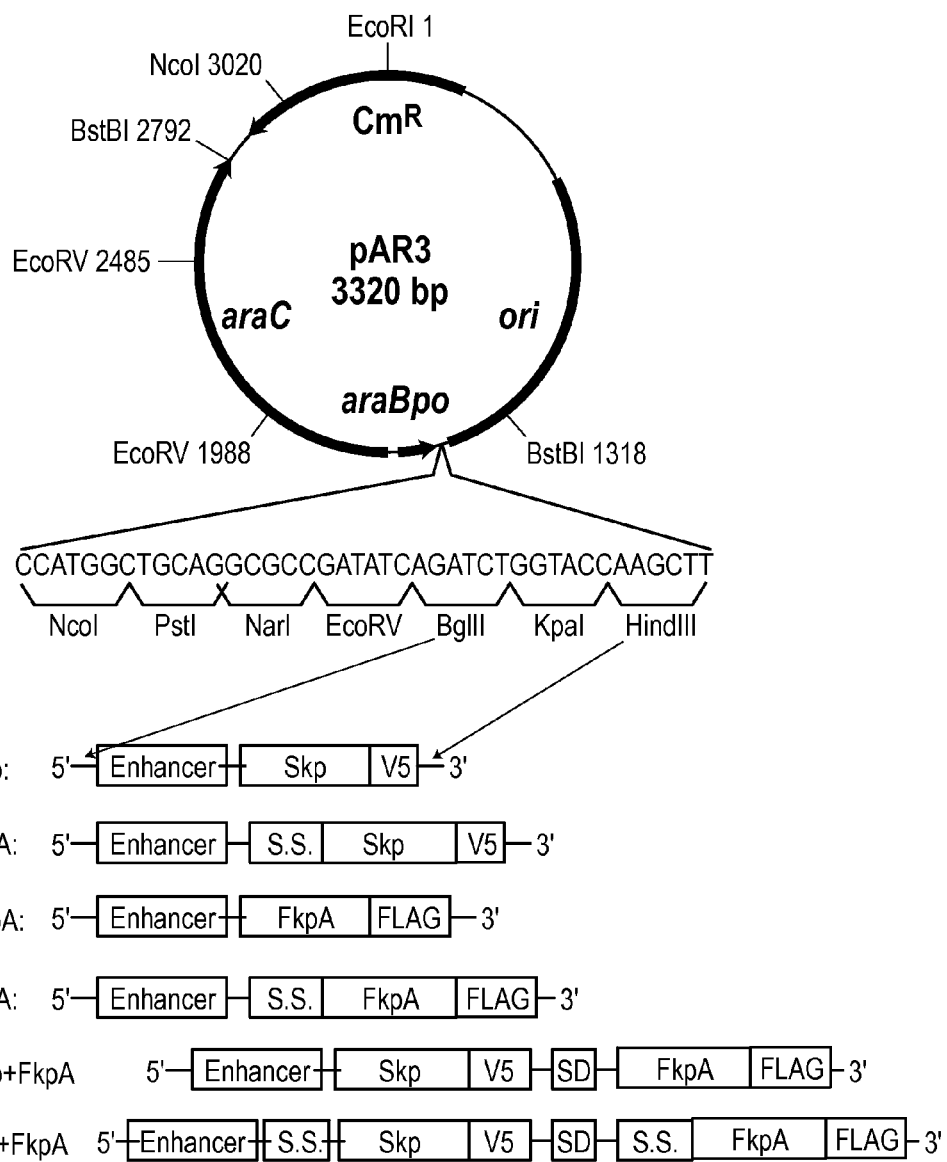
FIG. 1 is an illustration of FkpA and Skp constructs used in the experiments disclosed herein.

This disclosure relates to methods and materials useful for improving the yield of heterologously expressed proteins (e.g., antibodies) in prokaryotic cells (e.g., *E. coli* cells). The methods and materials in this disclosure relate to the discovery that expressing FkpA and/or Skp not linked to a functional signal sequence, such that FkpA and/or Skp localize in the cytoplasm of prokaryotic host cells, results in significantly improved yields of soluble, correctly folded and functional heterologous proteins secreted to the periplasm. One advantageous aspect of the invention is that phage display procedures can be performed more efficiently with phage produced in the host cells provided by the present disclosure. For example, rare antibodies with desirable antigen binding properties are more likely to be discovered using these host cells because the heterologous proteins displayed on the phage coat are more likely to be correctly folded and functional.

A. Definitions

As used herein, an antibody that "specifically binds" is "antigen specific", is "specific for" antigen or is "immunoreactive" with an antigen refers to an antibody that binds an antigen with greater affinity than other antigens of unrelated to similar sequence, preferably at least $10^3$, $10^4$, $10^5$, or $10^6$ greater affinity. In one aspect, the antibody of the invention, or fragments, variants, or derivatives thereof, will bind with a greater affinity to human antigen as compared to its binding affinity to similar antigens of other, i.e., non-human, species, but antibodies that recognize and bind orthologs are contemplated.

For example, an antibody or fragment thereof "specific for" its cognate antigen indicates that the variable regions of the antibodies recognize and bind the desired antigen with a detectable preference (e.g., where the desired antigen is a polypeptide, the variable regions of the antibodies are able to distinguish the antigen polypeptide from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody, for use in the methods of the invention are well known and routinely practiced in the art. For a comprehensive discussion of such assays, see Harlow et al. (Eds), Antibodies: A Laboratory Manual; Cold Spring Harbor Laboratory; Cold Spring Harbor, N.Y. (1988), Chapter 6. Antibodies for use in the invention can be produced using any method known in the art and described in greater detail herein.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous.

The term "derivative" when used in connection with polypeptides (e.g., proteins of interest, antibodies or antigen-binding fragments thereof) refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the invention.

"Detectable moiety" or a "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to another labeled nucleic acid molecule. The detectable moiety often generates a measurable signal, such as a radioactive, chromogenic, or fluorescent signal, that can be used to quantitate the amount of bound detectable moiety in a sample.

The term "host cell" is understood to refer not only to the particular subject cell or cells but also the progeny thereof. It is also understood that, during culture, natural or accidental mutations may occur in succeeding generations and thus such progeny may not be completely identical to the parent cell, but are still included within the scope of the term as used herein.

The term "operably linked" refers to a functional relationship between two or more polynucleotide (e.g., DNA) segments. Typically, it refers to the functional relationship of a regulatory control sequence, e.g., a transcriptional regulatory sequence, to a transcribed sequence. For example, a promoter/enhancer sequence, including any combination of cis-acting transcriptional control elements, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. A polylinker provides a convenient location for inserting coding sequences so the genes are operably linked to a promoter. Polylinkers are polynucleotide sequences that comprise a series of three or more closely spaced restriction endonuclease recognition sequences.

The term "signal sequence" refers to a polynucleotide sequence which encodes a short amino acid sequence (i.e., signal peptide) present at the $NH_2$-terminus of certain proteins that are normally exported by cells to noncytoplasmic locations (e.g., secretion) or to be membrane components. "Functional signal sequences" are capable of directing the transport of proteins from the cytoplasm to noncytoplasmic locations, such as the periplasm.

As used herein, the term "is not linked to a functional signal sequence" encompasses polypeptides in which the native signal sequence is removed or modified (e.g., mutated or truncated) to lack the function of directing transport of proteins from the cytoplasm to noncytoplasmic locations, and that have not been linked to a non-native functional signal sequence. The term thus encompasses embodiments wherein the polypeptide is encoded by a polynucleotide in which one or more codons encoding the signal sequence have been removed or mutated, as well as polynucleotides synthesized de novo such that one or more codons encoding the signal sequence are not incorporated.

The term "functional fragment" when used in reference to a polypeptide means a polypeptide that is truncated, i.e., missing one or more amino acids from the N-terminus or C-terminus, and that retains the desired activity. When used in reference to FkpA or Skp, "functional fragment" means a fragment that retains the ability to increase yield of functional heterologous protein. The term may analogously be applied to polynucleotides that are truncated.

The term "variant" when used in reference to a polypeptide means a polypeptide that has one or more substitutions, deletions or insertions relative to a parent polypeptide. In some contexts, the variant is one that retains the desired activity. When used in reference to FkpA or Skp, "functional variant" means a variant that retains the ability to increase yield of functional heterologous protein. The term may analogously be applied to polynucleotides that have one or more substitutions, deletions or insertions relative to a parent polynucleotide.

As used herein, the term "conservative amino acid substitution" is the replacement of one amino acid with another amino acid having similar properties, e.g. size, charge, hydrophobicity, hydrophilicity, and/or aromaticity, and includes exchanges as indicated below:

Original Exemplary
Ala (A) val; leu; ile
Arg (R) lys; gln; asn
Asn (N) gln; his; asp, lys; gln
Asp (D) glu; asn
Cys (C) ser; ala
Gln (O) asn; glu
Glu (E) asp; gln
Gly (G) ala
His (H) asn; gln; lys; arg
Ile (I) leu; val; met; ala; phe; norleucine
Leu (L) norleucine; ile; val; met; ala; phe
Lys (K) arg; gln; asn
Met (M) leu; phe; ile
Phe (F) leu; val; ile; ala; tyr
Pro (P) ala
Ser (S) thr
Thr (T) ser
Trp (W) tyr; phe
Tyr (Y) trp; phe; thr; ser
Val (V) ile; leu; met; phe; ala; norleucine Amino acid residues which share common side-chain properties are often grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

B. FkpA

FkpA (SEQ ID NO: 1) is expressed as a 270 amino acid protein. Amino acid residues 1-25 function as a signal sequence that is cleaved after directing secretion of FkpA into the periplasm, resulting in a 245 amino acid mature protein. The mature protein sequence is set forth in SEQ ID NO: 3 and corresponds to amino acids 26 through 270 of SEQ ID NO: 1. The chaperone activity resides in amino acid residues 26-140 and the peptidyl-prolyl isomerase activity resides in amino acid residues 141-270.

In example embodiments, a prokaryotic host cell of the disclosure comprises a polynucleotide encoding FkpA or a functional fragment or functional variant of FkpA that retains the ability to increase yield of functional heterologous protein, that is not linked to a functional signal sequence. In some or any embodiments, the functional fragment comprises amino acids 26-270 of SEQ ID NO: 1 or a fragment thereof that retains the ability to increase yield of functional heterologous protein. In some or any embodiments, the functional variant comprises an amino acid sequence at least 75%, 80%, 85%, 90% or 95% identical to at least 50 amino acids of residues 26-270 of SEQ ID NO: 1 that retains the ability to increase yield of functional heterologous protein.

In some or any embodiments, the functional fragment comprises amino acid residues 26 through 140 of SEQ ID NO: 1, the chaperone domain, or a fragment thereof that retains the ability to increase yield of functional heterologous protein, e.g., residues 40 through 140 of SEQ ID NO: 1. In example embodiments, the fragments are at least about 50, 55, 60, 65, 70, 75, 80, 85, 90, 95, 100, 105 or more amino acids in length. In some or any embodiments, the functional variants comprise an amino acid sequence at least 75%, 80%, 85%, 90% or 95% identical to at least 50 amino acids of residues 26-140, or 40-140 of SEQ ID NO: 1, that retain the ability to increase yield of functional heterologous protein. Such functional fragments and functional variants of the chaperone domain are referred to herein as a "chaperone domain fragment."

In some or any embodiments, the functional fragment comprises the peptidyl-prolyl isomerase domain of FkpA (i.e., amino acid residues 141 through 270 of SEQ ID NO: 1), or a fragment thereof that retains the ability to increase yield of functional heterologous protein, e.g., residues 141 through 249 of SEQ ID NO: 1. In example embodiments, the fragments are at least about 50, 55, 60, 65, 70, 75, 80, 85, 90, 95, 100, 105 or more amino acids in length. In some or any embodiments, the functional variants comprise an amino acid sequence at least 75%, 80%, 85%, 90% or 95% identical to at least 50 amino acids of residues 141-270, or 141-249, of SEQ ID NO: 1 that retain the ability to increase yield of functional heterologous protein. Such functional fragments and functional variants of the peptidyl-prolyl isomerase domain are referred to herein as a "peptidyl-prolyl isomerase domain fragment."

In some or any embodiments, the FkpA is an ortholog of SEQ ID NO: 1 from a different bacterial species. Examples include *Enterobacter cloacae* (Swiss-Prot Accession No. CBK86063), *Cronobacter sakazakii* (Swiss-Prot Accession No. YP001440409), *Klebsiella pneumoniae* (Swiss-Prot Accession No. YP002921574), *Citrobacter koseri* (Swiss-Prot Accession No. YP001456234), *Shigella flexneri* (Swiss-Prot Accession No. NP709121), *Shigella boydii* (Swiss-Prot Accession No. YP001882020), *Shigella dysenteriae* (Swiss-Prot Accession No. YP404977), *Escherichia albertii* (Swiss-Prot Accession No. ZP02904021), *Escherichia fergusonii* (Swiss-Prot Accession No. YP002384399), *Citrobacter rodentium* (Swiss-Prot Accession No. YP003367879), *Yersinia kristensenii* (Swiss-Prot Accession No. ZP04624699), *Erwinia tasmaniensis* (Swiss-Prot Accession No.

YP001909086), *Erwinia billingiae* (Swiss-Prot Accession No. YP003743520), *Edwardsiella tarda* (Swiss-Prot Accession No. YP003297282), *Sodalis glossinidius* (Swiss-Prot Accession No. YP455971), *Salmonella enterica* (Swiss-Prot Accession No. NP462357), and *Serratia odorifera* (Swiss-Prot Accession No. ZP06192651).

A sequence alignment of the above FkpA orthologs is provided in FIG. 13. Information from the sequence alignment can be used to generate functional variants and functional fragment variants of FkpA, as defined above. Techniques for deleting and mutating amino acids are well known in the art. See Ausubel, F. M. et al., *Current Protocols in Molecular Biology*, John Wiley & Sons, (1998), including all supplements through 2011. Generally, to construct functional variants, either non-conservative or conservative substitutions or deletions can be introduced at the positions that differ between species, as these positions tend to be permit non-conservative substitutions while retaining function. For positions with amino acid residues conserved across species, the residue is either retained or conservative substitutions are introduced. FkpA variants are tested for the ability to increase the yield of functional heterologous protein according to the methods disclosed herein.

C. Skp

Skp (SEQ ID NO: 2) is expressed as a 161 amino acid protein. Amino acid residues 1-20 function as a signal sequence that is cleaved after directing secretion of Skp into the periplasm, resulting in a 141 amino acid mature protein, that functions as a homotrimer. The mature protein sequence is set forth in SEQ ID NO: 4 and corresponds to amino acid residues 21 through 161 of SEQ ID NO: 2.

In example embodiments, a prokaryotic host cell of the disclosure comprises a polynucleotide encoding Skp, or a functional fragment or functional variant of Skp that retains the ability to increase yield of functional heterologous protein, that is not linked to a functional signal sequence. In some or any embodiments, the functional fragment comprises amino acids 21 through 161 of SEQ ID NO: 2 or a fragment thereof that retains the ability to increase yield of functional heterologous protein. In example embodiments, the fragments are at least about 50, 55, 60, 65, 70, 75, 80, 85, 90, 95, 100, 105, 110, 115, 120, 125, 130 or more amino acids in length. In some or any embodiments, the functional variants comprise an amino acid sequence at least 75%, 80%, 85%, 90% or 95% identical to at least 50 amino acids of residues 21-161 of SEQ ID NO: 2 that retains the ability to increase yield of functional heterologous protein.

In some or any embodiments, the Skp is an ortholog of SEQ ID NO: 2 from a different bacterial species.

A sequence alignment of Skp orthologs from different bacterial species can be used to generate functional variants of Skp, as defined above. Functional variants of Skp are generated in the same general manner as described for FkpA. Skp variants are tested for the ability to increase the yield of functional heterologous protein according to the methods disclosed herein.

D. Host Cells

In some or any embodiments, the host cell is a prokaryotic cell. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *S. typhimurium*, *Serratia*, e.g., *S. marcescans*, and *Shigella*, as well as Bacilli such as *B. subtilis* and *B. licheniformis* (e.g., *B. licheniformis* 41 P disclosed in DD 266,710 published Apr. 12, 1989), *B. megaterium*, *B. brevi*, *Pseudomonas* such as *P. aeruginosa*, and *P. fluorescens*, *Ralstonia*, e.g., *R. eutropha*, *Staphylococcus*, e.g. *S. carnosus*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. Another preferred *E. coli* host cell is the "leaky" strain CY15070 (Paluh et al., *Nucl. Acids Res.* 24; 14(20): 7851-60 (1986); (ATCC#47022)). These examples are illustrative rather than limiting. A host cell that a "leaky phenotype" refers to a cell with an altered cell envelope that permits release of periplasmic components into the extracellular medium. Extracellular recombinant protein production has several potential advantages, including simplicity of purification, avoidance of protease attack, and minimization of harmful impacts on the host cell caused by high level accumulation of recombinant proteins in the periplasmic space. A number of mutations (naturally arising or engineered) causing the "leaky" phenotype are known in the art (Ni and Chen, *Biotechnol. Lett.* 31: 1661-70 (2009)). For example, mutation or deletion of the lpp gene encoding Braun's lipoprotein has been shown to dramatically increase the permeability of the *E. coli* outer membrane (Ni et al, *Biotech. and Bioeng.* 97(6): 1347-56 (2007)).

E. Heterologous Proteins of Interest

1. Heterologous Proteins Prone to Misfolding and/or Aggregation

In example embodiments, the heterologous protein is associated with mis-folding or a slow folding rate in the absence of FkpA and Skp (or other chaperones). It is a common occurrence for a heterologous protein (such as a mammalian protein, e.g., an antibody) to be expressed in a prokaryotic cell at low levels or to aggregate into inclusion bodies. Such heterologous proteins include: growth factors (e.g. epidermal growth factor, insulin-like growth factor-1); blood clotting factors (e.g. anti-hemophilic factor); hormones (e.g., insulin, glucagon, growth hormone, somatotropin, erythropoietin); cytokines (e.g., interferons, interleukins; granuloctye colony-stimulating factor, granulocyte-macrophage colony-stimulating factor, CD86); chemokines (e.g., CCL3); receptors (e.g., chemokine receptors, tyrosine kinase receptors); enzymes (e.g., proteases, lipases, carbohydrases, chymosin, DNAase, prourokinase, arginine deaminase, cytosine deaminase, L-asparaginase); enzyme activators (e.g., tissue-type plasminogen activator); enzyme inhibitors (e.g, tissue inhibitors of metalloproteases); peptides (e.g., hirudin, neuregulin-1 fragments); antibody fragments (e.g., Fab fragments); protein scaffolds (e.g. Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-1β-lactamase, fibronectin type III domains, CTLA-4, T-cell resptors, knottins, neocarzinostatin, carbohydrate binding module 4-2, green fluorescent protein, thioredoxin); vaccines (e.g. influenza vaccines, anthrax vaccines such as rPA vaccines, hepatitis E virus vaccines such as ORF2 vaccines, human papilloma virus vaccines); toxins; and immunotoxins (Misawa and Kumagai, *Biopolymers* 51: 297-307 (1999); Zhang et al, *Protein Expr. Purif.* 25(1):105-13 (2002); Demain, *Trends in Biotech.* 18(1): 26-31 (2000); Gebauer & Skerra, *Curr. Opin. Chem. Biol.* 13:245-55 (2009); Gill & Damle, *Curr. Opin.*

Biotech 17: 653-58 (2006); Hosse et al, Protein Sci. 15:14-27 (2006); Skerra, *Curr. Opin. Biotech* 18: 295-3-4 (2007); Song et al, *PLoS ONE* 3(5): e2257 (2008); Vahedi et al, *Applied Biochem. and Biotech.* 157(3): 554-61 (2009); Hakim and Benhar, *MAbs.* 1(3): 281-87 (2009)). Domains or fragments of heterologous proteins would also benefit from the present invention.

Heterologous proteins that would benefit from the present invention can readily be screened. For example, a heterologous protein of interest can be expressed in a prokaryotic cell that is also expressing a reporter (such as LacZ) under the control of a stress-responsive promoter. The stress-responsive promoter will respond to the accumulation of misfolded protein aggregates. Suitable stress-responsive promoters include, but are not limited to, the promoters from the ibpAB, ybeD, yhgI and yrfGHI genes of *E. coli*. See Lesley et al., *Protein Eng,* 15(2):153-60 (2002). Furthermore, heterologous proteins that would benefit from the present invention can be identified using only the protein's amino acid composition as the basis for the prediction, since parameters such as charge average and turn-forming residue fraction have been shown to correlate with inclusion body formation in *E. coli*. (Wilkinson and Harrison, *Nat. Biotech.* 9, 443-448 (1991)).

2. Heterologous Proteins Requiring Cis-Trans Isomerization

Most proline residues in proteins energetically favor the trans conformation. Some proteins, however, require the cis conformation for function, and peptidyl-proyly cis-trans isomerases catalyze this conversion. Some important natural substrates of the prolyl isomerases are now known, e.g., the Gag polypeptide of the human immunodeficiency virus-1 virion, steroid receptors, and intracellular calcium release channels, demonstrating the great variety of prolyl isomerization functions in the living cell (Göthel et al, *Cell. Mol. Life. Sci.* 55(3):423-36 (1999). Thus, in example embodiments, the heterologous protein is proline isomerization-dependent for proper folding and/or function. In one embodiment, the proline isomerization-dependent heterologous protein comprises an antibody or antibody fragment comprising a variable light (kappa) chain (Vκ).

3. Antibodies and Antibody Fragments

In example embodiments, the heterologous protein is an antibody. The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include: Fab, Fab', F(ab')2, Fv, domain antibody (dAb), Fcab™, complementarity determining region (CDR) fragments, single-chain antibodies (scFv), single chain antibody fragments, antibody molecules containing just two CDRs linked by a framework region, e.g., $V_H CDR1-V_H FR2-V_L CDR3$ fusion peptides, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camel-ized antibody, a VHH containing antibody, or a variant or a derivative thereof, and polypeptides that contain at least a portion of an immunoglobulin that is sufficient to confer specific antigen binding to the polypeptide, such as one, two, three, four, five, or six CDR sequences, as long as the antibody retains the desired biological activity.

In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, (*J. Mol. Biol.* 196:901-917, 1987); Chothia et al., (*Nature* 342:878-883, 1989).

The hypervariable region of an antibody refers to the CDR amino acid residues of an antibody which are responsible for antigen-binding. The hypervariable region comprises amino acid residues from a CDR (residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)) and/or those residues from a hypervariable loop (residues 26-32 (L1), 50-52 (L2) and 91-96 (L3) in the light chain variable domain and 26-32 (H1), 53-55 (H2) and 96-101 (H3) in the heavy chain variable domain as described by Chothia et al., *J. Mol. Biol.* 196: 901-917 (1987).

Framework or FR residues are those variable domain residues other than the hypervariable region residues.

"Heavy chain variable region" as used herein refers to the region of the antibody molecule comprising at least one complementarity determining region (CDR) of said antibody heavy chain variable domain. The heavy chain variable region may contain one, two, or three CDRs of said antibody heavy chain.

"Light chain variable region" as used herein refers to the region of an antibody molecule, comprising at least one complementarity determining region (CDR) of said antibody light chain variable domain. The light chain variable region may contain one, two, or three CDRs of said antibody light chain, which may be either a kappa or lambda light chain depending on the antibody.

Antibodies or antibody fragments with kappa light chain variable regions (Vκ) are especially suited for the methods and materials described herein. Vκ domains have cis-prolines (L8 and L95 by Kabat numbering). Moreover, the slow isomerization of the peptide bond preceding Pro-L95 is important because it must be cis for the formation of the native $V_H/V_L$ interface. In fact, the cis,trans isomerization of Pro-L95 is the rate limiting step for correct docking of $V_L$ and $V_H$. Lack of proper peptidyl-prolyl isomerization can drive the formation of off-pathway folding intermediates that promote aggregation.

Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody of the invention, if it comprises a constant domain, may be of any of these subclasses or isotypes, or a variant or consensus sequence thereof, or a hybrid of different isotypes (e.g., IgG1/IgG2 hybrid).

In exemplary embodiments, an antibody of the invention can comprise a human kappa (κ) or a human lambda (λ) light chain or an amino acid sequence derived therefrom, or a hybrid thereof, optionally together with a human heavy chain or a sequence derived therefrom, or both heavy and light chains together in a single chain, dimeric, tetrameric (e.g., two heavy chains and two light chains) or other form.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the natural antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of an antigen to which it binds. Accordingly, a "neutralizing" antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In some embodiments, the antibody is purified, e.g., (1) to greater than 95% by weight of antibody as determined by the Lowry method, and preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

F. Vectors

The vectors of the present invention generally comprise regulatory control sequences, e.g., transcriptional or translational control sequences required for expressing the exogenous polypeptide. Suitable regulatory control sequences include but are not limited to replication origin, promoter, enhancer, repressor binding regions, transcription initiation sites, ribosome binding sites, translation initiation sites, and termination sites for transcription and translation.

In some or any embodiments, the polynucleotides encoding FkpA that is not linked to a functional signal sequence and Skp that is not linked to a functional signal sequence are present on the same vector. In some embodiments, when present on the same vector, the polynucleotides are arranged such that they form an operon, i.e., transcription of the polynucleotides will generate a polycistronic messenger RNA. In some or any embodiments, the polynucleotides encoding FkpA that is not linked to a functional signal sequence and/or Skp that is not linked to a functional signal sequence, and the polynucleotide encoding the heterologous protein linked to a functional signal sequence are present on the same vector. In some embodiments, when present on the same vector, the polynucleotides encoding cytoplasmic FkpA and/or Skp, and the polynucleotide encoding the heterologous protein are arranged such that they form an operon. In some embodiments, a polynucleotide encoding cytoplasmic FkpA, a polynucleotide encoding a variable region light chain, and a polynucleotide encoding a variable region heavy chain are operatively linked to the same regulatory sequence (i.e., they form an operon). As will be appreciated by a person of skill in the art, each FkpA- and Skp-encoding polynucleotide will have suitable regulatory control sequences to allow for appropriate expression in the host cell.

1. Origins of Replication

The origin of replication (generally referred to as an ori sequence) permits replication of the vector in a suitable host cell. The choice of ori will depend on the type of host cells that are employed. Where the host cells are prokaryotes, the expression vector typically comprises an ori directing autonomous replication of the vector within the prokaryotic cells. Non-limiting examples of this class of ori include pMB1, pUC, as well as other bacterial origins.

2. Signal Sequences

In some or any embodiments, the host cell comprises a polynucleotide encoding a heterologous protein for recombinant production, wherein the heterologous protein is linked to a functional signal sequence. Signal sequences directing fusion polypeptides for periplasmic secretion in bacterial cells include those derived from spA, phoA, ribose binding protein, pelB, ompA, ompT, dsbA, torA, torT, and tolT (de Marco, *Microbial Cell Factories*, 8:26 (2009)). The pelB signal sequences disclosed in U.S. Pat. Nos. 5,846,818 and 5,576,195 are incorporated by reference in their entirety.

Also included within the scope of the invention are signal sequences derived from eukaryotic cells that also function as signal sequences in prokaryotic host cells (e.g., *E. coli*). Such sequences are disclosed in U.S. Pat. No. 7,094,579, the content of which is incorporated by reference in its entirety. Watson (*Nucleic Acids Research* 12:5145-5164 (1984)) discloses a compilation of signal sequences. U.S. Pat. No. 4,963,495 discloses the expression and secretion of mature eukaryotic protein in the periplasmic space of a host organism using a prokaryotic secretion signal sequence DNA linked at its 3' end to the 5' end of the DNA encoding the mature protein. Chang et al. (*Gene* 55:189-196 (1987)) discloses the use of the STII signal sequence to secrete hGH in *E. coli*. Gray et al. (*Gene* 39:247-245 (1985)) disclose the use of the natural signal sequence of human growth hormone and the use of the *E. coli* alkaline phosphatase promoter and signal sequence for the secretion of human growth hormone in *E. coli*. Wong et al. (*Gene*, 68:193-203 (1988)) disclose the secretion of insulin-like growth factor 1 (IGF-1) fused to LamB and OmpF secretion leader sequences in *E. coli*, and the enhancement of processing efficiency of these signal sequences in the presence of a prlA4 mutation. Fujimoto et al. (*J. Biotech.* 8:77-86 (1988)) disclose the use of four different *E. coli* enterotoxin signal sequences, STI, STII, LT-A, and LT-B for the secretion of human epidermal growth factor (hEGF) in *E. coli*. Denefle et al. (*Gene* 85:499-510 (1989)) disclose the use of OmpA and PhoA signal peptides for the secretion of mature human interleukin 1β. Content of all of the above documents is incorporated by reference in its entirety.

3. Selectable Markers

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, kanamycin, neomycin, G418, methotrexate, etc.; (b) complement auxotrophic deficiencies; or (c) supply critical nutrients not available from complex media. The choice of the proper selectable marker gene will depend on the host cell, and appropriate genes for different hosts are known in the art.

The vectors encompassed by the invention can be obtained using recombinant cloning methods and/or by chemical synthesis. A vast number of recombinant cloning techniques such as PCR, restriction endonuclease digestion and ligation are well known in the art. One of skill in the art can also use the sequence data provided herein or that in the public or proprietary databases to obtain a desired vector by any synthetic means available in the art. Additionally, using well-known restriction and ligation techniques, appropriate sequences can be excised from various DNA sources and integrated in operative relationship with the exogenous sequences to be expressed in accordance with the present invention.

G. Phage Display

The materials and methods of the disclosure are also useful in phage display techniques. *E. coli* cells expressing cytoplasmic FkpA and/or Skp, and functional fragments and functional variants thereof as described herein, enhance the efficiency of phage display, resulting in identification of rare clones. In some embodiments, prokaryotic host cells (e.g., *E. coli* cells) of the disclosure are used to screen phage display libraries.

Construction of phage display libraries, including libraries constructed from phagemid vectors, exploits the bacteriophage's ability to display peptides and proteins on their surfaces, i.e., on their capsids. Often, filamentous phage such as M13, fl or fd are used. Filamentous phage contain single-stranded DNA surrounded by multiple copies of major and minor coat proteins, e.g., pIII. A protein of interest may be fused to a fragment of a coat protein, for example pIII. Phagemid vectors comprising sequence coding for pIII fragments may be used along with helper phage to construct a phage display library. Coat proteins are displayed on the capsid's outer surface. DNA sequences inserted in-frame with capsid protein genes are co-transcribed to generate fusion proteins or protein fragments displayed on the phage surface. Peptide phage libraries thus can display peptides representative of the diversity of the inserted genomic sequences. Significantly, these epitopes can be displayed in natural folded conformations. The peptides expressed on phage display libraries can then bind target molecules, i.e., they can specifically interact with binding partner molecules such as antibodies (Petersen *Mol. Gen. Genet.* 249:425-31 (1995)), cell surface receptors (Kay, *Gene* 128:59-65) (1993), and extracellular and intracellular proteins (Gram, *J. Immunol. Methods* 161:169-76 (1993)).

The concept of using filamentous phages, such as M13, fd or fl, for displaying peptides on phage capsid surfaces was first introduced by Smith, *Science* 228:1315-1317 (1985). Peptides have been displayed on phage surfaces to identify many potential ligands (see, e.g., Cwirla, *Proc. Natl. Acad. Sci. USA* 87:6378-6382 (1990)). There are numerous systems and methods for generating phage display libraries described in the scientific and patent literature (see, e.g., Sambrook and Russell, Molecule Cloning: A Laboratory Manual, 3rd edition, Cold Spring Harbor Laboratory Press, Chapter 18, 2001; "Phage Display of Peptides and Proteins: A Laboratory Manual, Academic Press, San Diego, 1996; Crameri, *Eur. J. Biochem.* 226:53-58 (1994); de Kruif, *Proc. Natl. Acad. Sci. USA* 92:3938-42 (1995); McGregor, *Mol. Biotechnol.* 6:155-162 (1996); Jacobsson, *Biotechniques*, 20:1070-1076 (1996); Jespers *Gene* 173:179-181 (1996); Jacobsson, *Microbiol Res.* 152:121-128 (1997); Fack, *J. Immunol. Methods* 206:43-52 (1997); Rossenu, *J. Protein Chem.* 16:499-503 (1997); Katz, *Annu. Rev. Biophys. Biomol. Struct.* 26:27-45 (1997); Rader, *Curr. Opin. Biotechnol.* 8:503-508 (1997); Griffiths, *Curr. Opin. Biotechnol.* 9:102-108 (1998)).

Typically, exogenous nucleic acids encoding peptides or proteins to be displayed are inserted into a coat protein gene, e.g. gene III or gene VIII of the phage. The resultant fusion proteins may be displayed on the surface of the capsid. Protein VIII is present in approximately 2700 copies per phage, compared to 3 to 5 copies for protein III. Multivalent expression vectors, such as phage or phagemids, can be used for manipulation of exogenous genomic DNA or cDNAs and production of phage particles in bacteria (see, e.g., Felici, *J. Mol. Biol.* 222:301-310 (1991)).

Phagemid vectors are often employed for constructing the phage library. These vectors include the origin of DNA replication from the genome of a single-stranded filamentous bacteriophage, e.g., M13, fl or fd. A phagemid can be used in the same way as an orthodox plasmid vector, but can also be used to produce filamentous bacteriophage particle that contain single-stranded copies of cloned segments of DNA. Double-stranded T7 vectors can also be employed in which the displayed product on the mature phage particle is released by cell lysis.

An antibody or antibody fragment, e.g., a scFv, Fab or Fv may be displayed on the surface of a phage using phage display techniques. Exemplary antibody phage display methods are known to those skilled in the art and are described, e.g., in Hoogenboom, *Overview of Antibody Phage-Display Technology and Its Applications*, from METHODS IN MOLECULAR BIOLOGY ANTIBODY PHAGE DISPLAY: METHODS AND PROTOCOLS (2002) 178:1-37 (O'Brien and Aitken, eds., Human Press, Totowa, N.J.). For example, a library of antibodies or antibody fragments (e.g., scFvs, Fabs, dAbs, Fvs with an engineered intermolecular disulfide bond to stabilize the $V_H$-$V_L$ pair, and diabodies) can be displayed on the surface of a filamentous phage, such as the nonlytic filamentous phage fd or M13. Antibodies or antibody fragments with the desired binding specificity can then be selected.

A protein scaffold may be displayed on the surface of a phage using phage display techniques. Exemplary protein scaffold libraries include, but are not limited to, Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-1β-lactamase, fibronectin type III domains, CTLA-4, T-cell resptors, knottins, neocarzinostatin, carbohydrate binding module 4-2, green fluorescent protein, thioredoxin (Gebauer & Skerra, *Curr. Opin. Chem. Biol.* 13:245-55 (2009); Gill & Damle, *Curr. Opin. Biotech* 17: 653-58 (2006); Hosse et al, Protein Sci. 15:14-27 (2006); Skerra, *Curr. Opin. Biotech* 18: 295-3-4 (2007)).

H. Affinity Maturation

The materials and methods disclosed herein are also useful for affinity maturation. According to the invention, a large number of substitutional variants can be generated, displayed on the surface of a plurality of phage particles, and selected for the desired target-binding characteristics by contacting the phage particles with target protein. Affinity maturation generally involves preparing and screening polypeptide variants, e.g., antibody variants, that have substitutions within the CDRs of a parent polypeptide and selecting variants that have improved biological properties such as binding affinity relative to the parent polypeptide. A convenient way for generating such substitutional variants is affinity maturation. Briefly, several hypervariable region residues (e.g. 6-7 residues) are mutated to generate all possible amino substitutions at each site. The antibody variants thus generated are displayed in a monovalent fashion on the surface of a cell. The cell surface-displayed variants are then screened for their biological activity (e.g. binding affinity). See e.g., WO 92/01047, WO 93/112366, WO 95/15388 and WO 93/19172 for examples of phage display methods of affinity maturation.

Current antibody affinity maturation methods belong to two mutagenesis categories: stochastic and nonstochastic. Error prone PCR, mutator bacterial strains (Low et al., *J. Mol. Biol.* 260, 359-68 (1996)), and saturation mutagenesis (Nishimiya et al., J. Biol. Chem. 275:12813-20 (2000); Chowdhury, P. S. Methods Mol. Biol. 178, 269-85 (2002)) are typical examples of stochastic mutagenesis methods (Rajpal et al., *Proc Natl Acad Sci USA*. 102:8466-71 (2005)). Nonstochastic techniques often use alanine-scanning or site-directed mutagenesis to generate limited collections of specific variants. Available methods include: affinity maturation via panning methods, look-through mutagenesis, error-prone PCR, gene site saturation mutagenesis, targeted affinity maturation, and DNA shuffling (Huls et al, *Cancer Immunol Immunother.* 50:163-71 (2001); Zaccolo et al., *J. Mol. Biol.* 285:775-783 (1999); Kretz et al., *Methods Enzymol.* 388: 3-11 (2004); WO2009/088933; Stemmer, *Proc. Natl. Acad. Sci. USA*, 91:10747-51 (1994)).

I. Labels

In some embodiments, the cells and/or heterologous proteins are labeled to facilitate their detection. A "label" or a "detectable moiety" is a composition detectable by spectroscopic, photochemical, biochemical, immunochemical, chemical, or other physical means. For example, labels suitable for use in the present invention include, radioactive labels (e.g., $^{32}P$), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide. Other antigen-like tags such as FLAG tags, His tags, etc., are known in the art.

Examples of labels suitable for use in the present disclosure include, but are not limited to, fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.).

The label may be incorporated according to methods well-known in the art.

Means for detecting labels are well known to those of skill in the art. Thus, for example, where the label is radioactive, means for detection include a scintillation counter or photographic film, as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled heterologous proteins can be used in the diagnosis of a disease or health condition.

EXAMPLES

Example 1

Materials and Methods i. Construction of Plasmid Vectors Expressing the FkpA or Skp Chaperones XL1Blue cells (recA1 endA1 gyrA96 thi-1 hsdR17 supE44 relA1 lac [F' proAB lacIqZΔM15 Tn10 (Tetr)]) and TG1 cells (supE thi-1 Δ(lac-proAB) Δ(mcrB-hsdSM)5 (rK-mK-) [F' traD36 proAB lacIqZΔ15]) were purchased from Stratagene (now Agilent, Santa Clara, Calif.). For cytoplasmic expression of chaperones, the native signal sequences were deleted from the genes encoding the chaperones FkpA (SwissProt No. P65764) and Skp (SwissProt No. P0AEU7). For periplasmic expression of chaperones, the native signal sequences were included. To generate the plasmid constructs of the cytoplasmic or periplasmic versions of the chaperone Skp, FkpA, and the bicistronic Skp-FkpA, the chaperone gene fragments were amplified by PCR and then cloned into the plasmid vector pAR3 (ATCC No, 87026). The vector pAR3 (Pérez-Pérez et al, Gene, 1995, 158(1):141-2) contains the pBAD promoter and the cat gene which confers chloramphenicol antibiotic resistance. It also harbors the p15A origin of replication which is compatible with the origin of replication pBR322 (ColE1) used for the vectors coexpressing all Fabs or scFvs in the subsequent experiments. First, two different forward primers were designed in order to amplify FkpA from XL1Blue cells by PCR with or without the signal sequence together with one reverse primer. Similarly, two forward primers and one reverse primer were designed to amplify Skp from XL1Blue cells by PCR with or without the signal sequence.

To generate the monicistronic chaperone plasmid constructs pAR3-FkpA_per, pAR3-Skp_per (for periplasmic expression) and pAR3-FkpA_cyt, pAR3-Skp_cyt (for cytoplasmic expression), the products of the previous PCR reactions were used as templates for PCR reamplification using forward primers to incorporate a BglII restriction site followed by the enhancer sequence GAATTCATTAAAGAGGAGAAATTAACT upstream from the chaperone encoding gene fragment. Reverse primers were used to incorporate the V5 tag sequence (GGTAAGCCTATCCCTAACCCTCTCCTCGGTCTCGATTCTACG) into the pAR3-Skp_per and pAR3-Skp_cyt and the FLAG tag sequence (GACTACAAGGACGATGACGACAAG) into the pAR3-FkpA_per and pAR3-FkpA_cyt followed by the restriction site HindIII.

To generate the bicistronic periplasmic pAR3-Skp-FkpA_per and cytoplasmic pAR3-Skp-FkpA_cyt constructs, the monocistronic PCR products were reamplified. To reamplify Skp, forward primers were designed to incorporate BglII, followed by the enhancer GAATTCATTAAAGAGGAGAAATTAACT and the periplasmic or cytoplasmic versions of Skp. A reverse primer was designed that anneals to the entire V5 tag and to an optimized Shine-Dalgarno (SD) sequence driving the translation initiation of FkpA. To reamplify FkpA, forward primers were designed to anneal to the C-terminal portion of V5, the optimized SD, and the periplasmic or cytoplasmic versions of FkpA. A reverse primer was designed to anneal to the C-terminal portion of FkpA, the FLAG tag sequence and to add a HindIII restriction site. The Skp and FkpA PCR products were then gel purified using Qiagen gel extraction kits (Valencia, Calif.) and used as templates for an overlap extension PCR reaction using the external forward Skp primer and external reverse FkpA primers. FIG. 1 shows a schematic representation of the chaperone constructs.

Ligations of the BglII-HindIII digested PCR products to the BglII-HindIII digested pAR3 vectors were then electroporated into XL1Blue cells and the resulting constructs were confirmed by DNA sequencing.

ii. Construction of Plasmid Vectors Expressing Fabs

All Fabs and scFvs used for this work were cloned in phagemid vectors harboring a triple 6His-cmyc-V5 tag, the beta lactamase gene conferring ampicillin resistance and the pBR322 (ColE1) origin of replication that is compatible to the p15A origin of the pAR3 vector (backbone for chaperone-expressing vectors). Representative kappa Fabs used herein were a) XPA23 (anti IL1β, human), b) ING1 (anti-EpCAM, human), c) 83-7 (anti-human insulin receptor (huINSR), murine), d) CF1 (anti-TIE-1, human), and BM7-2 (specific for a kinase target, human). The lambda gastrin-specific Fabs used herein were a) A10, b) C10, c) D1, and d) E6. The antigen reagents huINSR, TIE1-Fc, and IL1β were purchased from R&D Systems (Minneapolis, Minn.).

iii. Preparation of Cytoplasmic and Periplasmic E. coli Extracts

TG1 electroporation competent cells were cotransformed with two plasmids: a) the chaperone expressing monocistronic vectors pAR3-FkpA_per, pAR3-Skp_per, pAR3-FkpA_cyt, pAR3-Skp_cyt, or the bicistronic vectors pAR3-Skp-FkpA_per, pAR3-Skp-FkpA_cyt together with b) the Fab expressing vectors (or the empty plasmid pAR3 that was used as a negative control).

To prepare cytoplasmic and periplasmic extracts expressing only the chaperones, TG1 cells harboring the empty pAR3 (negative control) or the monocistronic or bicistronic chaperone plasmid constructs were grown overnight at 37° C. in 2YT growth media supplemented with 34 chloramphenicol and 2% (w/v) glucose. They were then subcultured in 100 ml flasks at 37° C. until the $OD_{600}$ reached 0.5-0.6. The expression of the chaperones was then induced with 0.2% arabinose (w/v) at 30° C. overnight. At that point, the $OD_{600}$ was recorded and cultures were normalized to the same $OD_{600}$. Cells were then pelleted and resuspended in 10 ml ice-cold PPB sucrose buffer (Teknova, Hollister, Calif.) at 1:4 dilution. Following incubation at 4° C. for 1 hour, samples were centrifuged for 30 minutes and the supernatants containing the periplasmic extracts were collected. The pellets were resuspended in 10 ml Bugbuster™ solution (Novagen, Gibbstown, N.J.) and supplemented with 10 µl benzonase nuclease (Novagen), in order to reduce the viscosity of the lysates and one tablet of complete EDTA-free protease inhibitor cocktail (Roche, Indianapolis, Ind.). Following 1 hour incubation on ice, the lysates were centrifuged at 16,000 g for 20 minutes at 4° C. and supernatants containing the cytoplasmic extracts were collected.

To prepare periplasmic extracts of cells expressing Fabs together with the chaperones, TG1 cells harboring the Fab and chaperone plasmid constructs (or pAR3 alone used as negative control) were grown overnight at 37° C. in 2YT growth media supplemented with 34 µg/ml chloramphenicol, 100 µg/ml ampicillin and 2% (w/v) glucose. They were then subcultured in 100 ml flasks at 37° C. until the $OD_{600}$ reached 0.5-0.6. Thirty minutes after the addition of 0.2% arabinose (w/v), IPTG was added to a final concentration of 1 mM and incubated overnight at 30° C. At that point, the $OD_{600}$ was recorded and cultures were normalized to equal $OD_{600}$. Cells were then pelleted and resuspended in 10 ml ice-cold PPB sucrose buffer (Teknova) at 1:4 dilution and one tablet of complete EDTA-free protease inhibitor cocktail (Roche). Following incubation at 4° C. for 1 hour, samples were centrifuged for 30 minutes and the supernatants containing the periplasmic extracts were collected.

iv. Western Blotting

For Western blot analysis, samples (20 µl) of the periplasmic and cytoplasmic extracts were suspended in SDS loading buffer with 0.7M beta-mercaptoethanol, boiled, and then loaded in NuPAGE™ 4-12% Bis-Tris precast gels (Invitrogen, Carlsbad, Calif.) using NuPAGE MOPS SDS running buffer (Invitrogen). Proteins from the reduced gels were then transferred to PVDF membranes using the Millipore-SNAP-i.d.™ electroblotter (Millipore Corp., Bedford, Calif.). Membranes were blocked with 0.5% bovine serum albumin (BSA)/phosphate buffered saline (PBS) and incubated for 15 min at room temperature with mouse anti-V5 antibodies (Sigma, St. Louis, Mo.) (for skp detection) at 1:2,000 or with mouse-anti-FLAG primary antibodies (Sigma) at 1:1,000 dilution in 0.5% BSA/PBS followed by goat anti-mouse IgG (H+L) conjugated with horseradish peroxidase (Jackson Immunoresearch, West Grove, Pa.) at a 1:2,000 dilution. Color was developed with 1-Step TMB-Blotting substrate solution (Pierce, Thermo Fisher Scientific, Rockford, Ill.).

v. ELISA a. Target ELISA

The amount of functional Fab was determined by ELISA. Maxisorp™ 96-well plates (Nunc, Rochester, N.Y.) were coated with 3 µg/ml or 1 µg/ml antigen at 50 µl/well (see details below) diluted in phosphate buffer saline (PBS). EpCAM (binds ING-1 Fab), IL1β (binds XPA23 Fab) and TIE1-Fc (binds CF1 Fab) were coated at 3 µg/ml. Kinase target (binds the BM7-2 Fab) was coated at 2 µg/ml. Human insulin receptor (huINSR) (binds the 83-7 Fab) was coated at 1 µg/ml. Biotinylated gastrin (14-mer peptide recognized by the A10, C10, D1, E6 Fabs) was coated at 1 µg/ml diluted in PBS on Reacti-Bind™ Streptavidin-coated 96-well plates (Thermo Scientific, Minneapolis, Minn.). Coated plates were incubated overnight at 4° C. and then blocked with 5% non-fat dry milk (Carnation, Nestle, Ohio) in PBS buffer (350 µl/well) (no blocking was required for the streptavidin-coated plates). Plate washes were carried out in PBS with 0.05% Tween 20. Serial dilutions of the Fabs, primary and secondary antibodies were done in 5% non-fat dry milk in PBS. Diluted Fabs (50 µl/well) were allowed to bind to their blocked antigens for 1 hour at room temperature. The presence of the ING1, XPA23, CF1, BM7-2, A10, C10, D1, E6 Fabs was confirmed using goat-anti-human IgG (specific for $F(ab')_2$) (Jackson Immunoresearch) primary antibody at 1:2,000 dilution, followed by donkey anti-goat IgG (H+ L) conjugated with horseradish peroxidase (Santa Cruz Biotechnology, Santa Cruz, Calif.) at 1:10,000 dilution. The presence of the 83-7 Fab was detected using rabbit-anti-mouse IgG [specific for $F(ab')_2$] (Jackson Immunoresearch) primary antibody at 1:2,000 dilution, followed by goat anti-rabbit IgG (H+L) conjugated with horseradish peroxidase (Jackson Immunoresearch) at 1:10,000 dilution. The assay was developed by the addition of TBD soluble substrate (CALBIOCHEM, La Jolla, Calif.). The reaction was quenched by the addition of 50 µl of 4.5 N $H_2SO_4$ and read at 405 nm by a SPECTRAmax Plus™ microplate reader (Molecular Devices, Sunnyvale, Calif.).

b. Expression ELISA

The amount of total Fab was determined by ELISA. For the detection of ING1, XPA23, BM7-2 and CF1 human kappa Fabs, Maxisorp™ 96-well plates (Nunc, Thermo Scientific) were coated with 50 µl/well of 3 µg/ml goat-anti-human kappa (Invitrogen, Carlsbad, Calif.) diluted in phosphate buffer saline (PBS). For the detection of 83-7 murine kappa Fabs, Maxisorp™ 96-well plates were coated with 50 µl/well of 3 µg/ml goat-anti-mouse kappa antibodies (Jackson Immunoresearch) diluted in phosphate buffer saline (PBS). For the detection of the human lambda A10, C10, D1, and E6 Fabs, 96-well high binding assay Maxisorp™ 96-well plates were coated with 50 µl/well of 3 µg/ml goat-anti-human lambda (Pierce, Rockford, Ill.) diluted in phosphate buffer saline (PBS). Coated plates were incubated overnight at 4° C. and then blocked with 5% non-fat dry milk (Carnation, Nestle, Ohio) in PBS buffer (350 µl/well) (no blocking was required for the streptavidin-coated plates). Plate washes were carried out in PBS with 0.05% Tween 20. Serial dilutions of the Fabs, primary and secondary antibodies were done in 5% non-fat dry milk in PBS. Diluted Fabs (50 µl/well) were allowed to bind to their blocked antigens for 1 hour at room temperature. The presence of the Fabs was detected using rabbit-anti-V5 (Sigma) primary antibody at 1:2,000 dilution, followed by goat anti-rabbit IgG (Fc specific) conjugated with horseradish peroxidase (Jackson Immunoresearch) at 1:10,000 dilution. The assay developed by the addition of TBD soluble substrate (CALBIOCHEM, La Jolla, Calif.). The reaction was quenched by the addition of 50 µl of 4.5 $NH_2SO_4$ and read at 450 nm by a SPECTRAmax Plus™ microplate reader (Molecular Devices, Sunnyvale, Calif.).

vi. Surface Plasmon Resonance

Quantitation of human Fab in periplasmic extracts was determined by Surface Plasmon Resonance (SPR) on the Biacore 2000 instrument (GE Healthcare). Fabs were quantified using goat-anti-human IgG [specific for $F(ab')_2$] (Jackson Immunoresearch Cat #109-006-097) immobilized at a high density on a Biacore CMS Sensor chip (GE Healthcare Cat #BR-1000-12). A standard curve was generated by diluting human Fab (Jackson Immunoresearch Cat #009-000-007) in two fold serial dilutions into assay running buffer and served for the estimation of the Fab concentrations. Data analysis was performed using BIAevaluation software V4.1 (GE Healthcare, Piscataway, N.J.).

The concentration of active ING1 Fab bound to the antigen EpCAM and its specific activity ([ligand bound (RU)]/[Fab captured(RU)]×[MW(Fab)/MW(ligand)]×100) were estimated by immobilizing the same amount of Fab (coexpressed or not with cytFkpA) on a goat-anti-human IgG [specific for $F(ab')2$] surface followed by the injection of 2 µg/ml EpCAM.

vii. scFv and Fab Naïve Phage Display Libraries; Selections and Rescue a. Panning and Rescue Kinase target was biotinylated with Sulfo-NHS-LC-Biotin (Pierce, Rockford, Ill.) using the manufacturer's protocol and 10-fold molar excess of biotin reagent. The biotinylation of kinase was confirmed by SPR. The biotinylated reagent was then used to pan scFv and Fab naïve phage display libraries.

For the first round of phage panning using a kappa scFv naïve library, $4.5 \times 10^{12}$ colony forming units (cfu) of phage particles were used. For the first round of phage panning using a Fab naïve library, $1.5 \times 10^{13}$ cfu of phage particles of a Fab lambda library or $1 \times 10^{13}$ cfu of phage particles of a Fab kappa library were blocked for 1 hour at RT in 1 ml of 5% non-fat dry milk (Carnation, Nestle, Ohio) in PBS buffer with gentle rotation. Thus, two separate panning selections, one from the Fab-kappa and one from the Fab-lambda libraries, were performed.

Blocked phages were twice deselected for 30 minutes against streptavidin-coated magnetic Dynabeads® M-280

(Invitrogen Dynal AS, Oslo, Norway). For the 1st, 2nd and 3rd rounds of selection, 200, 50 and 10 pmoles of biotinylated kinase reagent were used, respectively. The biotin-kinase was then incubated with blocked streptavidin-coated magnetic Dynabeads® M-280 for 1 hour with gentle rotation in order to immobilize the biotin-kinase and remove unbiotinylated material. Kinase-captured beads were then washed twice with PBS. The deselected phage were incubated with the biotin-kinase streptavidin beads for 90 minutes at room temperature.

For the first round of panning, beads were quickly washed (i.e., beads were pulled out of solution using a magnet and resuspended in 1 ml wash buffer) three times with PBS-0.05% Tween, followed by three times with PBS. For the second round of panning, beads were quickly washed six times with PBS-0.05% Tween followed by a single 10 minute wash in 1 ml wash buffer at room temperature with gentle rotation with PBS-0.05% Tween and then six times with PBS followed by one 10 minute wash with PBS. For the third round of panning, beads were quickly washed six times with PBS-0.05% Tween, followed by four washes for five minutes with PBS-0.05% Tween and then six quick washes with PBS, followed by four 5 minute washes with PBS. The kinase-bound phage were eluted via incubation for 30 minutes with 100 mM triethylamine (TEA) at room temperature and subsequently neutralized with 1M Tris-HCl (pH 7.4). The phage eluted from the first and second rounds of panning were used to infect TG1 E. coli cells when the $OD_{600}$ was equal to 0.5. Phage output from the third round of panning was divided into two aliquots. Half of it was used to infect TG1 cells alone grown in 2YT media and the second half was used to infect TG1 cells expressing the cytoplasmic chaperone FkpA (from plasmid pAR3-FkpA-_cyt) grown in 2YT media supplemented with 34 ug/ml chloramphenicol.

Following infection for 1 hour at 37° C. while shaking at 90 rpm, cells were centrifuged and pellets resuspended in 2YT growth media supplemented with 100 μg/ml ampicillin and 2% (w/v) glucose. Resuspended cells then were plated on 2YT agar plates containing 100 ug/ml carbenicillin and 2% glucose and incubated overnight at 30° C. Similarly, TG1 cells expressing the chaperone FkpA were plated on 2YT agar plates with 100 ug/ml carbenicillin, 34 ug/ml chloramphenicol and 2% glucose and incubated overnight at 30° C.

Phage was rescued with helper phage M13K07 at a multiplicity of infection (MOI)~20. For this purpose, third round selection output clones were allowed to grow to an $OD_{600}$~0.5. At that point, cells were infected with the helper phage at 37° C. for 1 hour while shaking at 100 rpm. Cell pellets were resuspended in 2YT media supplemented with 100 ug/ml ampicillin and 50 ug/ml kanamycin and allowed to grow overnight at 25° C. Phage in the supernatant were recovered by centrifugation and used for the next round of panning. In order to estimate the enrichment resulting from the phage selections, the amount of input and output phage were titered and plated on 2YT agar plates supplemented with the appropriate antibiotics.

b. Generation of Periplasmic Extracts from Library-Selected Antibody Clones

Individual TG1 colonies were picked and grown in 2YT supplemented with 100 ug/ml ampicillin and 0.1% (w/v) glucose at 37° C. Fab or scFv expression was then induced with 1 mM IPTG when the $OD_{600}$ reached a value of 0.5. Induction continued overnight at 30° C.

Similarly, individual TG1 clones harboring the plasmid that expresses cytoplasmic FkpA were picked from the third round of selection output and grown in 2YT growth media supplemented with 100 μg/ml ampicillin, 34 μg/ml chloramphenicol and 0.1% (w/v) glucose at 37° C. In order to express FkpA, arabinose was added when the $OD_{600}$ reached 0.5 at 30° C. Thirty minutes following the addition of arabinose, 1 mM IPTG was added to induce the expression of Fabs or scFvs and the incubation continued overnight at 30° C.

Bacterial periplasmic extracts were prepared according to standard methods using ice-cold PPB solution at 1:4 dilution (Teknova) in double distilled water (ddH2O) supplemented with EDTA-free protease inhibitor cocktail tablets (Roche, Ind.). The resulting lysate supernatants (periplasmic extracts) were assayed by ELISA, as described below.

c. ELISA Screening of Antibody Phage Clones

ELISA Maxisorp® plates were coated overnight at 4° C. with 2 ug/ml kinase reagent in PBS. Plates were then blocked for 1 hour at RT with 350 ul/well of 5% milk/PBS. Bacterial periplasmic extracts were also blocked with 5% non-fat dry milk for 1 hour and then loaded to the ELISA plate (50 ul/well) and allowed to bind to the coated kinase for 2 hours at RT. An anti-kinase mAb was used as a positive ELISA screening control. ELISA-bound antibody fragments were detected with murine anti-V5 antibodies (Sigma) at 1:2,000 dilution for 1 hour at RT followed by goat anti-mouse IgG (H+L) conjugated with horse-radish peroxidase (Jackson Immunoresearch) at 1:10,000 dilution. Three washes with PBS-0.05% Tween-20 (Teknova) were performed following every stage of the ELISA screens. The positive control mAb was detected by goat anti-human IgG (H+L) conjugated with horseradish peroxidase for 1 hour at room temperature. The assay developed by the addition of TBD soluble substrate (CALBIOCHEM). The reaction was quenched by the addition of 50 ul of 4.5 $NH_2SO_4$ and read at 450 nm by a SPECTRAmax Plus microplate reader (Molecular Devices).

Example 2 i. Enhancement of Expression of Fabs and scFvs in the Periplasm of E. coli

Figure 2A:
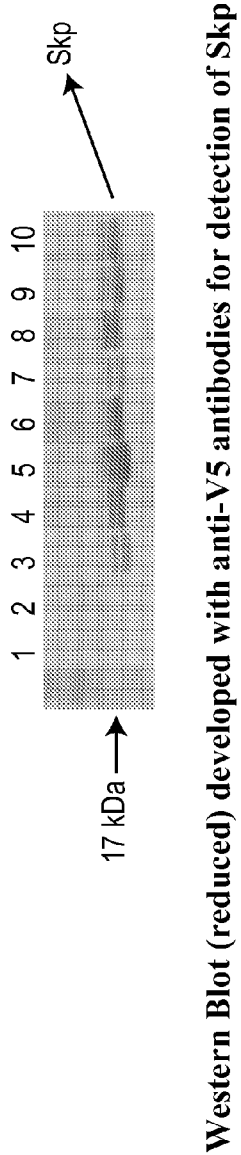
FIG. 2 illustrates the various Skp (FIG. 2A) and FkpA (FIG. 2B) constructs expressed in *E. coli* and detected by Western blot.
Figure 2B:
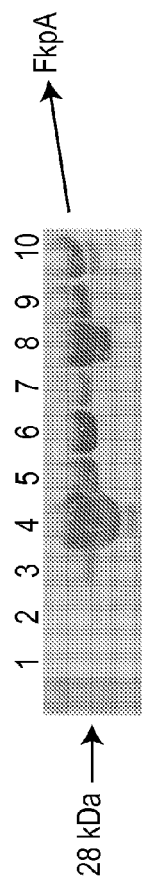
Figure 3:
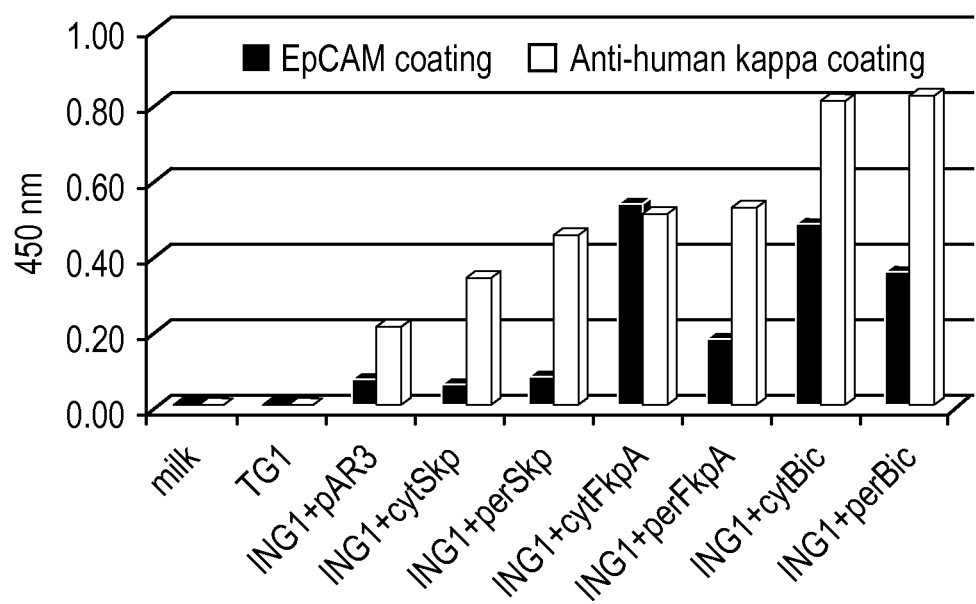
FIG. 3 illustrates the results of an ELISA to detect the total amount (grey bars) of the anti-EpCAM ING1 Fab or the functional (black bars) ING1 Fab expressed in *E. coli* strains expressing various combinations of FkpA and Skp constructs. "cytSkp" indicates Skp without a signal sequence (i.e., cytoplasmic Skp). Similarly, "cytFkpA" indicates FkpA expressed without a signal sequence (i.e., cytoplasmic FkpA). "perSkp" and "perFkpA" indicate Skp and FkpA expressed with their signal sequences (i.e., periplasmic Skp or FkpA). "cytBic" indicates cytoplasmic expression of both FkpA and Skp from a bicistronic message. "perBic" indicates periplasmic expression of both FkpA and Skp from a bicistronic message.

Periplasmic expression of kappa and lambda light chain Fab fragments upon the coexpression of the E. coli peptidyl prolyl cis/trans isomerase FkpA, the E. coli molecular chaperone Skp, and the bicistronic Skp-FkpA was investigated. In order to enable expression of the chaperones in the E. coli periplasm or cytoplasm, the genes encoding the chaperones were amplified by PCR from the E. coli chromosome of XL1Blue cells with or without their native signal sequences. The PCR products were then cloned into the expression vector pAR3. The periplasmic and cytoplasmic Skp-FkpA bicistronic products were generated by overlap extension PCR and cloned into pAR3. The chaperone plasmids were first transformed by electroporation into E. coli TG1 cells and periplasmic, as well as cytoplasmic, extracts were generated, as described in Example 1. The expression of the chaperones in TG1 cells was then tested by Western Blotting using anti-V5 and anti-FLAG tag antibodies to detect the presence of Skp and FkpA (see FIG. 2A, 2B). Skp, FkpA and the bicistronic Skp-FkpA were successfully expressed without their periplasmic signal sequences (see (−) sign) in the E. coli cytoplasmic extracts and with their periplasmic signal sequences (see (+) sign) in the E. coli periplasmic extracts. Not surprisingly, due to the leakiness of the E. coli inner membrane during the preparation of the periplasmic and cytoplasmic extracts, small amounts of Skp and FkpA without their leader sequences could also be found in the bacterial periplasm and small amounts of Skp and FkpA with their leader sequences could also be found in the cytoplasm.

a. Fabs with Kappa Light Chains:

First, the human kappa light chain anti-EpCAM ING1 Fab was expressed in TG1 with or without the monocistronic or bicistronic chaperone constructs. The total amount of Fab expressed in the periplasm and the amount of active Fab binding the protein EpCAM was assessed by expression and target ELISAs, respectively. In expression ELISAs, anti-kappa coated antibodies were used to detect the Fab light chains. The Fab heavy chains were then detected by antibodies recognizing the V5 tag on the C-terminus of $CH_1$ (see FIG. 3, grey columns). In target ELISAs, Fab-specific polyclonal antibodies were used to identify the functional antibodies that are able to recognize the coated EpCAM antigen (see FIG. 3, black columns).

These ELISA results demonstrate that the expression of functional ING1 Fab is substantially increased when it is coexpressed with the cytoplasmic (signal sequence-less) version of FkpA (sixth black column from the left). It is also interesting that the entire Fab amount expressed with the presence of cytoplasmic FkpA (sixth grey column from the left) is functional.

Similarly, the human light kappa chain anti-IL1β XPA23 Fab was expressed in TG1 with or without the monocistronic or bicistronic chaperone constructs. The total amount of Fab expressed in the periplasm and the amount of active Fab binding the protein IL1β was assessed by expression (FIG. 4, grey columns) and target ELISAs (FIG. 4, black columns), respectively.

Figure 4:
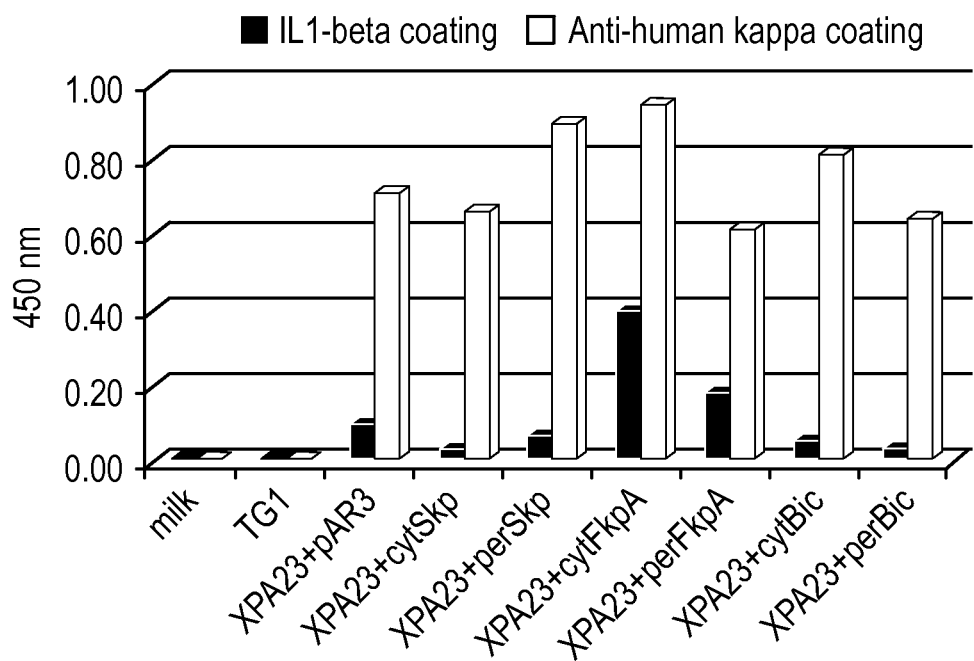
FIG. 4 illustrates the results of an ELISA to detect the total amount (grey bars) of the anti-IL1 XPA23 Fab or the functional (black bars) XPA23 Fab expressed in *E. coli* strains expressing various combinations of FkpA and Skp constructs. Skp and FkpA constructs are as described above for FIG. 3.

These ELISA results demonstrate that the expression of functional XPA23 Fab is substantially increased when it is coexpressed with the cytoplasmic (signal sequence-less) version of FkpA (FIG. 4, sixth black column from the left). These results also indicate that the vast majority of the total amount of Fab expressed with or without the presence of the chaperones (with the exception of the cytoplasmic FkpA) is non-functional.

Figure 5A:
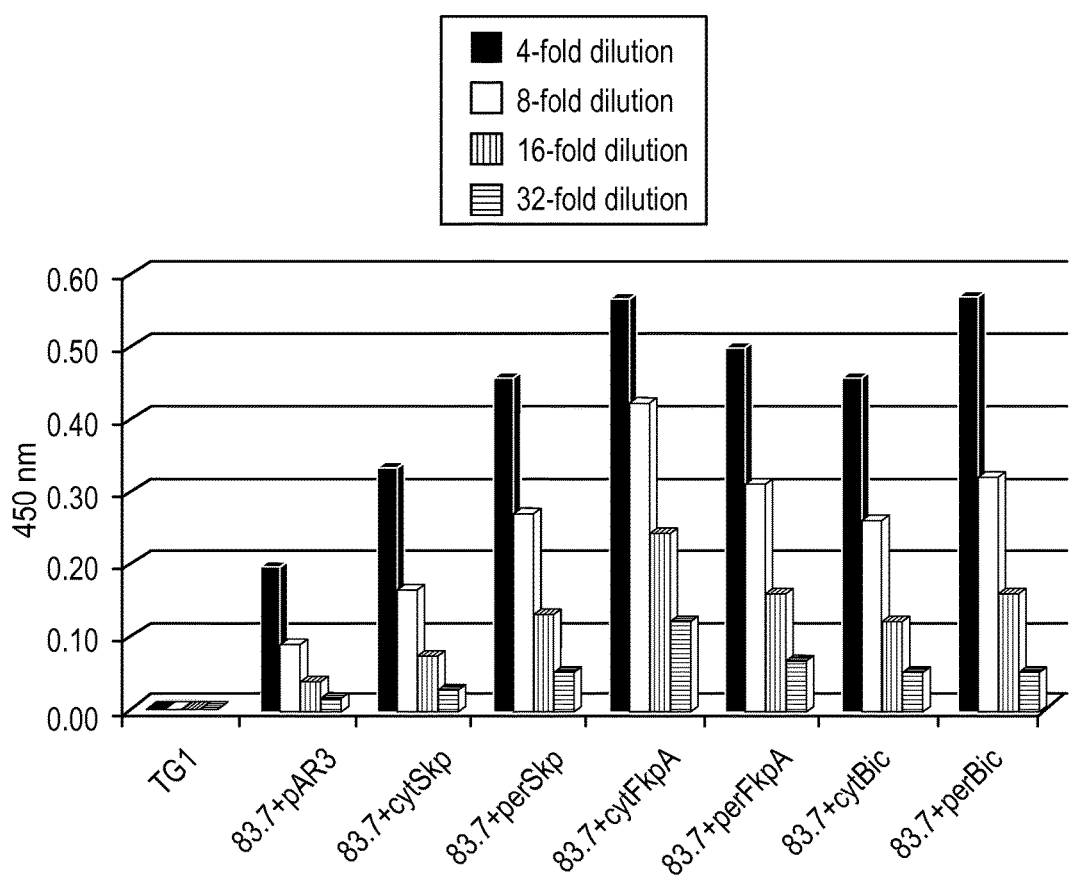
Figure 5B:
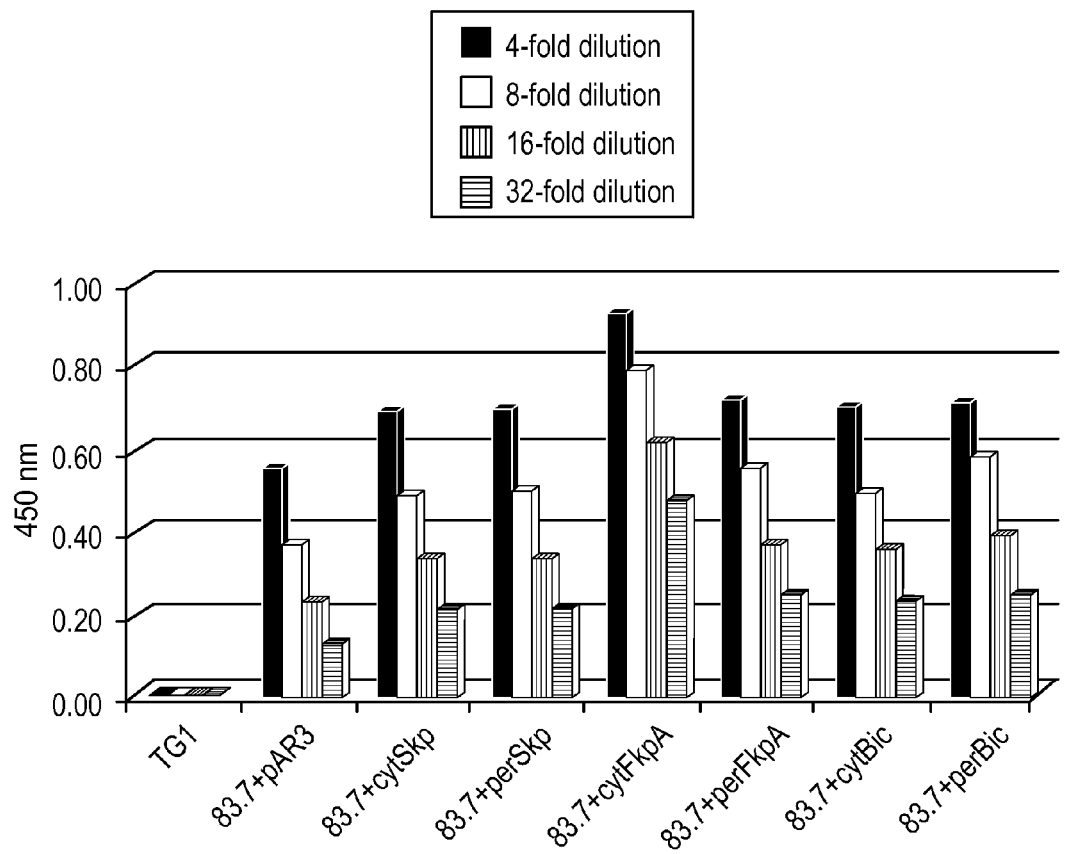
FIG. 5B is an antibody dilution series detecting functional 83-7 Fab. Skp and FkpA constructs are as described above for FIG. 3.

The murine light kappa anti-human insulin receptor (hu-INSR) 83-7 Fab was expressed in TG1 with or without the monocistronic or bicistronic chaperone constructs. The total amount of Fab expressed in the periplasm and the amount of active Fab binding huINSR was assessed by expression (FIG. 5A) and target ELISAs (FIG. 5B), respectively. Serial 83-7 Fab antibody dilutions were performed.

These results show that the active 83-7 Fab yield is improved due to the concomitant expression of the cytoplasmic FkpA (fifth stack of columns from the left).

Figure 6A:
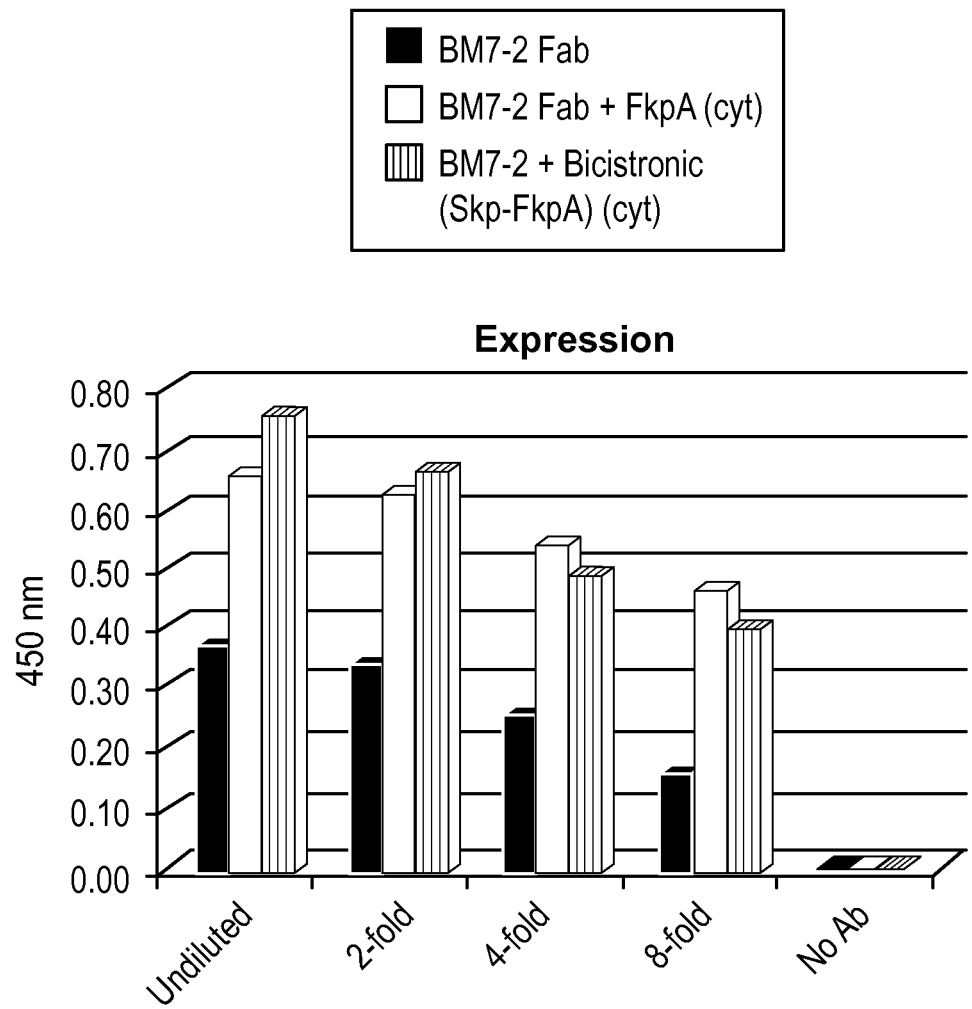
Figure 6B:
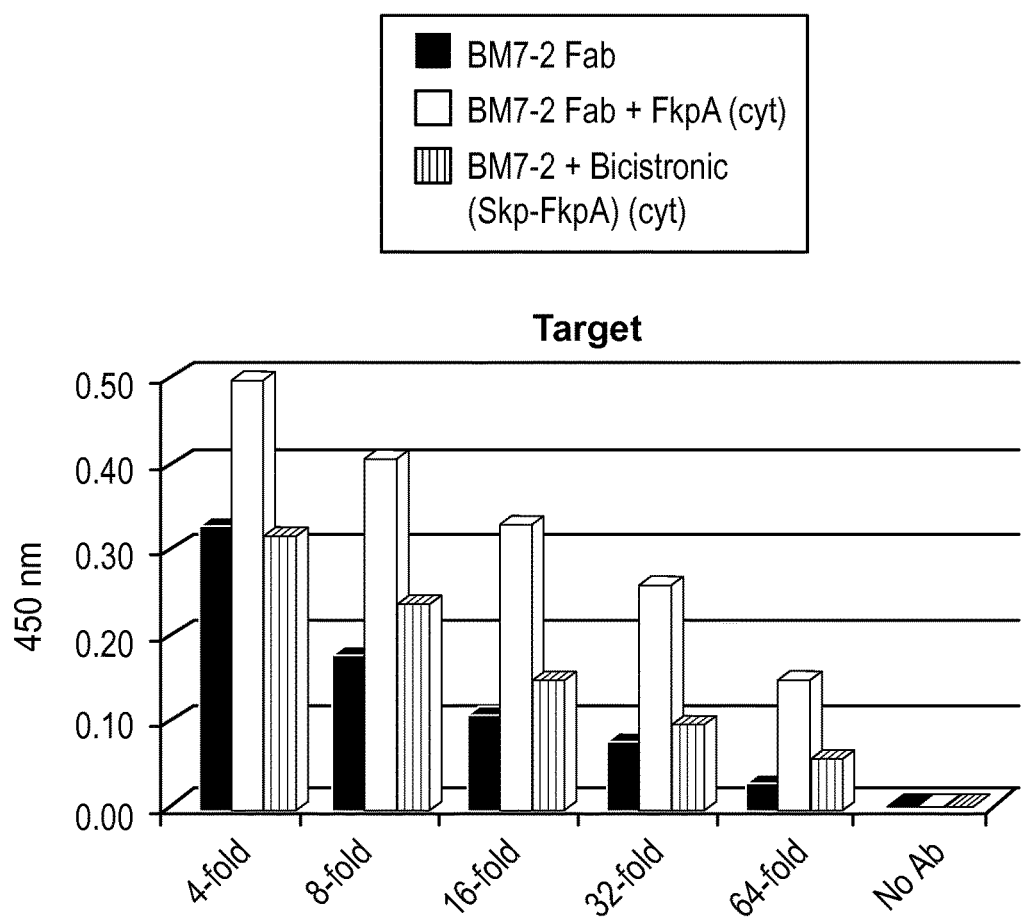
FIG. 6B is an antibody dilution series detecting functional BM7-2 Fab.

The human kappa BM7-2 Fab which recognizes kinase target was expressed in TG1 with or without the cytoplasmic versions of FkpA and Skp-FkpA. As previously described, the total periplasmic Fab and the antigen-binding active Fab was tested by expression (FIG. 6A) and target ELISAs (FIG. 6B), respectively. Three (FIG. 6) or five (FIG. 6B) antibody dilutions were performed.

These results demonstrate the significant enhancement of total BM7-2 Fab expression with both cytoplasmic FkpA alone, as well as with the bicistronic construct expressing both Skp and FkpA in the cytoplasm of *E. coli*. However, there is a substantial increase of the active Fab upon coexpression of the cytoplasmic FkpA alone.

Figure 7:
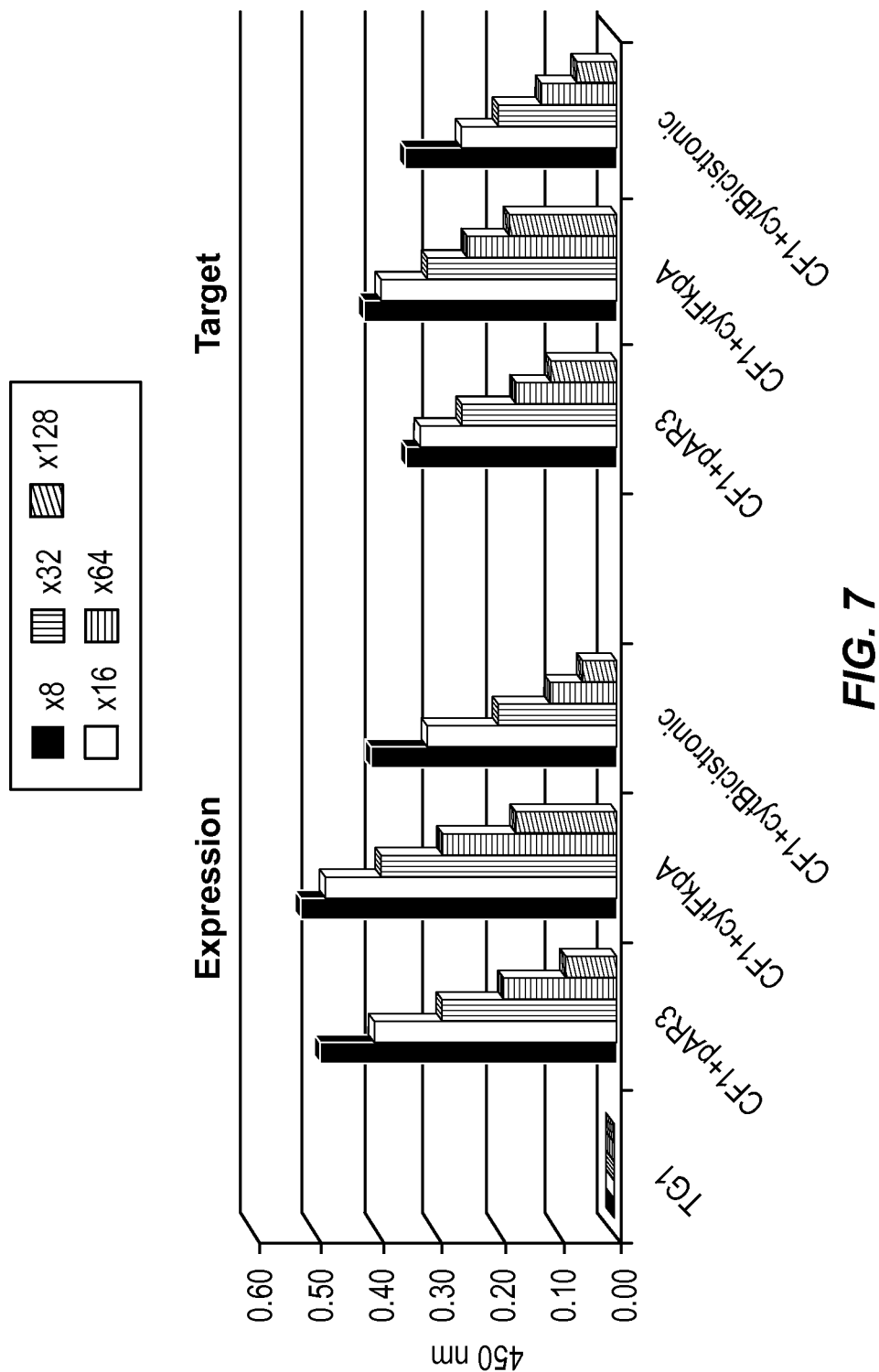
FIG. 7 illustrates the results of an ELISA to detect the total amount of the anti-gastrin human kappa anti-TIE1-Fc Fab CF1 or the functional CF1 Fab expressed in *E. coli* strains expressing cytoplasmic FkpA or both cytoplasmic FkpA and cytoplasmic Skp constructs. "Expression ELISA" is an antibody dilution series detecting the total amount of CF1 Fab produced while "Target ELISA" is an antibody dilution series detecting functional CF1 Fab.

The anti-TIE1-Fc Fab CF1 was coexpressed in TG1 with or without the monocistronic FkpA and bicistronic Skp-FkpA cytoplasmic constructs. The total and functional Fab yields were then tested by expression (FIG. 7, first four sets of columns from the left) and target ELISAs (FIG. 7, last three sets of columns from the left), respectively. Five antibody dilutions were performed.

These ELISA results show that cytoplasmic FkpA improves the expression of functional CF1 in the *E. coli* periplasm.

b. Fabs with Lambda Light Chains

Figure 8A:
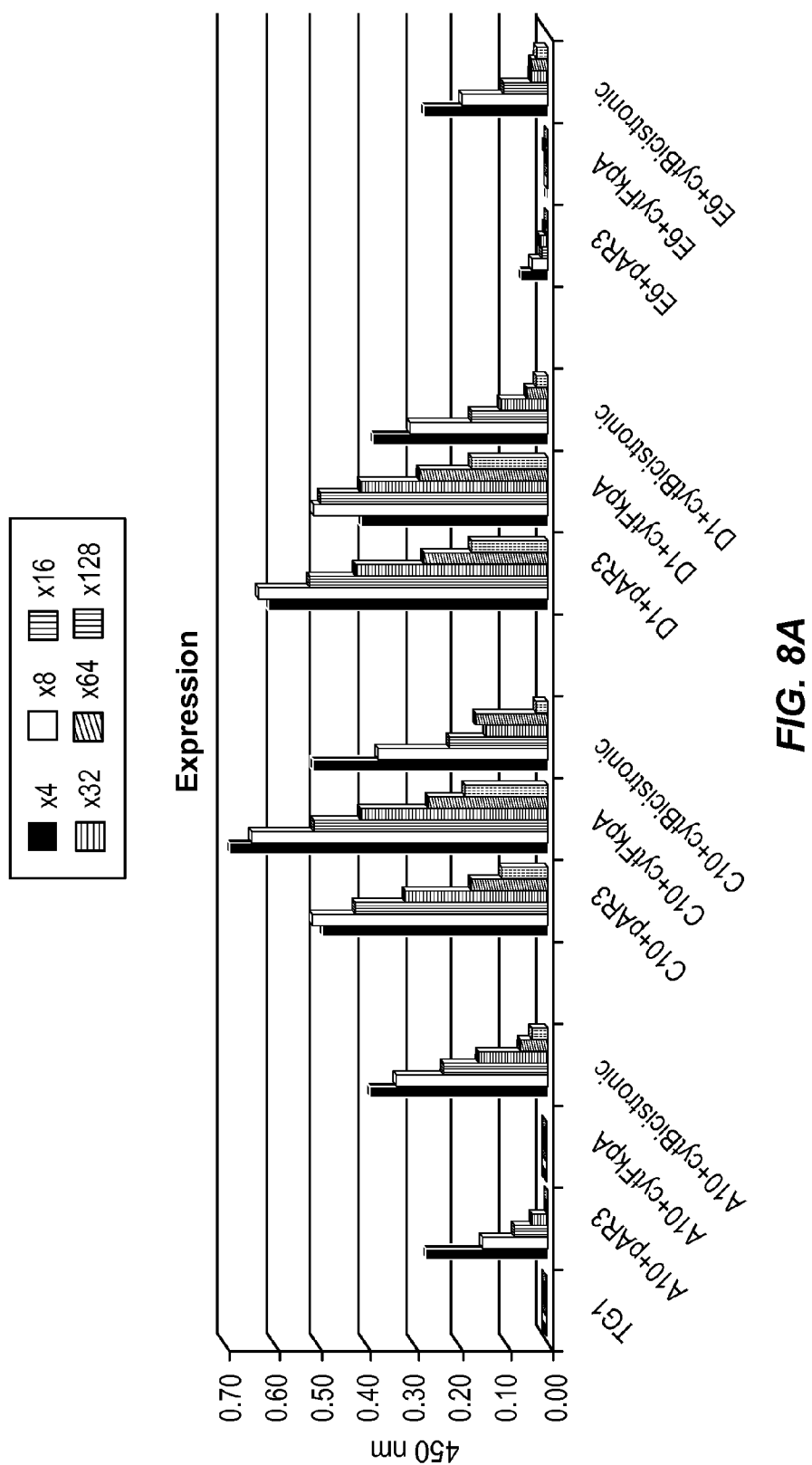
Figure 8B:
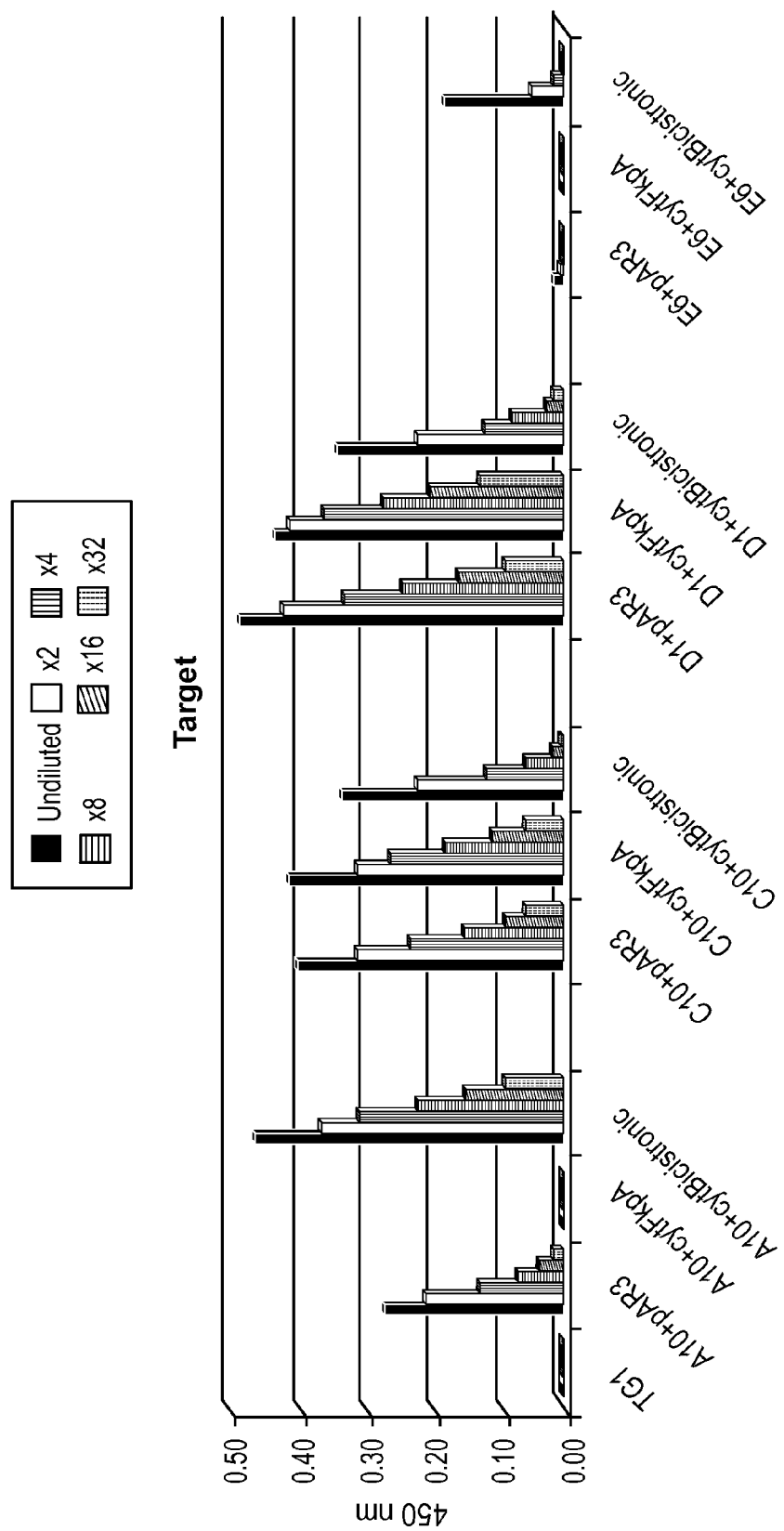
FIG. 8B is an antibody dilution series detecting functional Fab.

The expression of total and active human anti-gastrin lambda light chain-containing Fabs A10, C10, D1, and E6 in the TG1 *E. coli* periplasm with the presence of cytoplasmic FkpA, Skp and Skp-FkpA was assessed by ELISA. To determine total Fab expression, anti-lambda antibodies were first coated on the plate. Subsequently, the Fab heavy chains were probed by antibodies recognizing the V5 tag on the C-terminus of CH1 (see FIG. 8A). To identify the relative amounts of functional Fabs specifically binding gastrin, Fab-specific polyclonal antibodies were used (see FIG. 8B). Serial Fab dilutions were used for both ELISAs.

Unlike Fabs with kappa light chains that include proline residues in cis conformation, the effect of FkpA on the expression yields of active lambda light chain Fabs (that do not have cis Pro residues) is less apparent. Our results show that only the C10 and D1 Fab expression appeared to benefit slightly from the overexpression of cytoplasmic FkpA. FkpA did not influence the expression of E6, which was undetectable when no chaperones were coexpressed. Interestingly, the coexpression of FkpA in the cytoplasm of TG1 abolished expression of the A10 Fab in the TG1 periplasm. The effects of the molecular chaperone function of FkpA on the expression of Fabs containing lambda light chains appear to be more unpredictable than the effects on Fabs containing kappa light chains. Importantly, our study demonstrated that the expression of A10 was substantially improved and that of E6 was dramatically rescued following the coexpression of the cytoplasmic bicistronic Skp-FkpA. These results indicate that the cytoplasmic Skp accounts for the enhancement of the active protein yields of A10 and E6 Fabs, where FkpA failed to assist.

Figure 9:
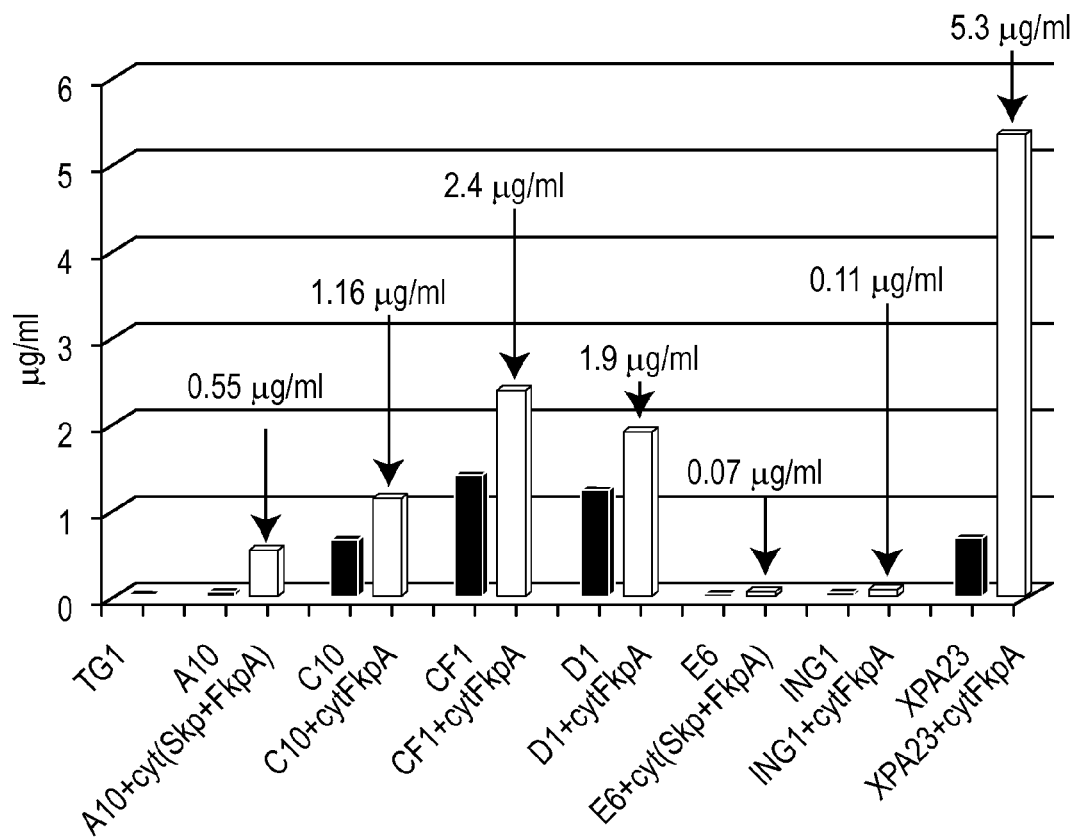
FIG. 9 illustrates the results of a surface plasmon resonance assay to calculate the actual yields of the indicated Fabs produced in *E. coli* strains expressing various FkpA and Skp constructs, as indicated.

In order to calculate the actual Fab protein yields upon the coexpression of Skp, FkpA or the bicistronic Skp-FkpA, surface plasmon resonance was employed, using an anti-human Fab sensor chip that captures the human Fabs. The periplasmic extracts of human Fabs coexpressed with the chaperone versions that resulted in the most profound protein yield improvements were tested, based on the previous ELISA results. A standard curve was first generated using a control human Fab and protein concentrations were then estimated based on SPR resonance units (RUs) (see FIG. 9).

ii. Effect of Cytoplasmic FkpA on the Expression of scFv and Fab Phage Libraries a. Kappa Fab Library Our results unexpectedly showed that coexpression of cytoplasmic FkpA enhances the expression of functional kappa light chain Fabs (and certain lambda Fabs) in the *E. coli* periplasm. Subsequently, we tested the ability of FkpA to improve the expression of naïve Fab or scFv libraries that were selected by phage display. First, three rounds of phage panning selections were performed against the biotinylated kinase target using a kappa Fab naïve phage display library, as described in Example 1. Following the third round of panning, 93 output clones were picked and allowed to grow in a 96-well plate. Induction of Fab expression was performed as previously described and periplasmic extracts were tested for binding to target antigen by ELISA, as described in Example 1 (see FIG. 10A). In all plates, wells A1 and A2 were negative controls and well H12 was a positive control. Ninety-three additional output clones following the third round of panning were picked and were induced to express the Fab fragments together with the cytoplasmic FkpA. Expression of active Fab in the bacterial periplasm was assessed by ELISA (see FIG. 10B).

We conclude that overexpression of cytoplasmic FkpA improves the kappa light chain Fab expression yields in the *E. coli* periplasm because six positive clones were identified, compared to none in the absence of the chaperone.

b. Lambda Fab Library

Similarly, third round clones were chosen and tested following panning with a Fab lambda chain library. ELISA screening of Fab periplasmic extracts in TG1 cells identified 32 clones binding to the kinase target (FIG. 11A). Following coexpression of the cytoplasmic FkpA, 26 binders were identified. The level of expression (see FIG. 11B) was clearly higher in the presence of FkpA.

c. Kappa ScFv Library

Phage selection was also performed using a naïve XOMA kappa scFv library against the kinase target. ELISA screening of scFv periplasmic extracts identified 65 positive (and stronger) binders when scFv was coexpressed with the cytoplasmic FkpA (see FIG. 12B). In the absence of the chaperone, only 26 weaker binders were identified (see FIG. 12A).

Thus, coexpression of the cytoplasmic version of the PPIase FkpA dramatically increases a) the number, and b) the expression of antibody candidates selected from a kappa scFv phage library.

Example 3 i. Expression of Cytoplasmic Fkp Increases Hit Diversity and Expression when Panning a Phage Display Library For the first round of phage panning using a naïve Fab library, $1.6 \times 10^{13}$ cfu of phage particles of a Fab lambda library and $2.2 \times 10^{13}$ cfu of phage particles of a Fab kappa library were blocked for 1 hour at RT in 3.5 ml of 5% non-fat dry milk (Marvel, Premier Foods, UK) in PBS buffer with gentle rotation. Blocked phage were twice deselected for 45 minutes against streptavidin-coated magnetic Dynabeads® M-280 (Invitrogen Dynal AS, Oslo, Norway). TIE2, which was biotinylated with Sulfo-NHS-LC-Biotin (Pierce, Rockford, Ill.) using the manufacturer's protocol and 20-fold molar excess of biotin reagent and confirmed by ELISA, was incubated with blocked streptavidin-coated magnetic Dynabeads® M-280 for 45 minutes with gentle rotation in order to immobilize the biotin-TIE2 and remove unbiotinylated material. TIE2-captured beads were then washed twice with PBS. For the first, second and third rounds of selection, 100, 50 and 10 pmoles of biotinylated TIE2 were used, respectively. For the first round, the deselected phage were divided into two aliquots: one was used to infect TG1 cells, the other was used to infect TG1 cells harboring pAR3-FkpA_cyt. The rescued, deselected phage were used to perform parallel first round pannings by incubation with biotin-TIE2 streptavidin beads for 90 minutes at room temperature. The input phage for rounds two and three were generated with separate rescues from either the round one TG1 infection or the round one TG1 with pAR3-FkpA_cyt.

For the first round of panning, beads were washed for 5 minutes (i.e., beads were pulled out of solution using a magnet and resuspended in 1 ml wash buffer and rotated gently for 5 minutes) three times with PBS-0.05% Tween, followed by three times with PBS. For the second round of panning, beads were washed for 5 minutes six times with PBS-0.05% Tween followed by six 5-minutes washes with PBS. For the third round of panning, beads were washed for 5 minutes eight times with PBS-0.05% Tween followed by eight 5-minutes washes with PBS. The TIE2-bound phage were eluted via incubation for 30 minutes with 100 mM triethylamine (TEA) at room temperature and subsequently neutralized with 1M Tris-HCl (pH 7.4). The phage eluted from each round of panning were used to infect either TG1 *E. coli* cells or TG1 with pAR3-FkpA_cyt when the $OD_{600}$ was equal to 0.5. TG1 cells were grown in 2YT media and TG1 cells expressing the cytoplasmic chaperone FkpA (from plasmid pAR3-FkpA_cyt) were grown in 2YT media supplemented with 34 µg/ml chloramphenicol.

Following infection for 1 hour at 37° C., cells were centrifuged and pellets resuspended in 2YT growth media supplemented with 100 µg/ml carbenicillin and 2% (w/v) glucose. Resuspended cells then were plated on 2YT agar plates containing 100 µg/ml carbenicillin and 2% glucose and incubated overnight at 30° C. Similarly, TG1 cells expressing the chaperone FkpA were plated on 2YT agar plates with 100 µg/ml carbenicillin, 34 µg/ml chloramphenicol and 2% glucose and incubated overnight at 30° C.

Phage was rescued with helper phage M13K07 at a multiplicity of infection (MOI)~20. For this purpose, first and second round selection output clones were allowed to grow to an $OD_{600}$-0.5. At that point, cells were infected with helper phage at 37° C. for 1 hour while shaking at 100 rpm. Cell pellets were resuspended in 2YT media supplemented with 100 µg/ml carbenicillin and 50 µg/ml kanamycin and allowed to grow overnight at 25° C. Phage in the supernatant were recovered by centrifugation and used for the next round of panning. In order to estimate the enrichment resulting from the phage selections, the amount of input and output phage were titered and plated on 2YT agar plates supplemented with the appropriate antibiotics.

The generation of periplasmic extracts and ELISA screening was done according to the protocols in Example 1 with biotin-TIE2 coated on Reacti-Bind™ Streptavidin-coated 96-well plates, which do not require blocking. Competition ELISA was performed to approximate the affinities of individual clones. The protocol for the competition ELISA was similar to the screening ELISA above except that non-biotinylated TIE2 was added to the blocked periplasmic extracts at 0, 1, 10, and 100 nM concentrations and allowed to incubate for 1 hour before it was added to the ELISA plate. The OD at 450 nm for each concentration of TIE2 was compared to the OD at 450 nm when no TIE2 was added to the periplasmic extracts. The lowest concentration of TIE2 mixed with the periplasmic extracts which competed with the binding of the Fab to the TIE2-biotin coated on the plate (ratio of A450 with TIE2 to A450 without TIE2<0.6) was indicative of affinity of the antibody fragment in the periplasmic extract (Sidhu et al, *JMB*, 338:299-310 (2004); Deshayes et al, *Chem. & Biol.*, 9:495-505 (2002)).

Figure 14:
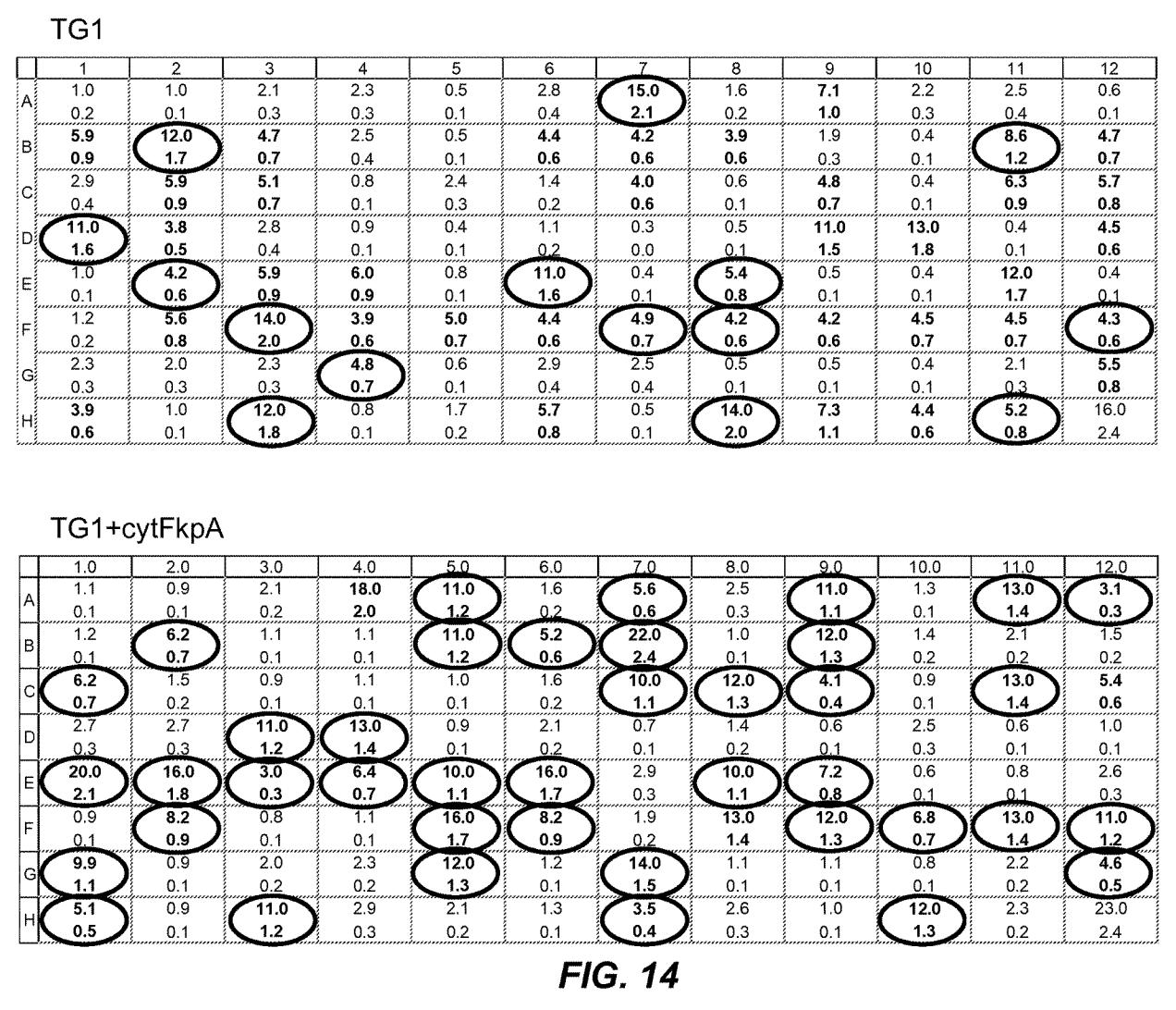

From each panning arm, TG1 or TG1 expressing cytoplasmic FkpA (TG1+cytFkpA), 93 clones were screened for binding to TIE2. The TG1 and TG1+cytFkpA panning produced an almost equal number of hits ($OD_{450}$>3-fold above background signal), 47 and 43, respectively. However, the hits from the TG1+cytFkpA panning appeared to express better, as 40% of these hits had an $OD_{450}$ greater than 12-fold above background, while for the TG1 hits, only 15% were more than 12-fold above background. The TG1+cytFkpA panning also had greater diversity with 40 of the 47 clones being unique antibody fragments versus only 15 of 47 clones for the TG1 panning (FIG. 14).

Figure 15:
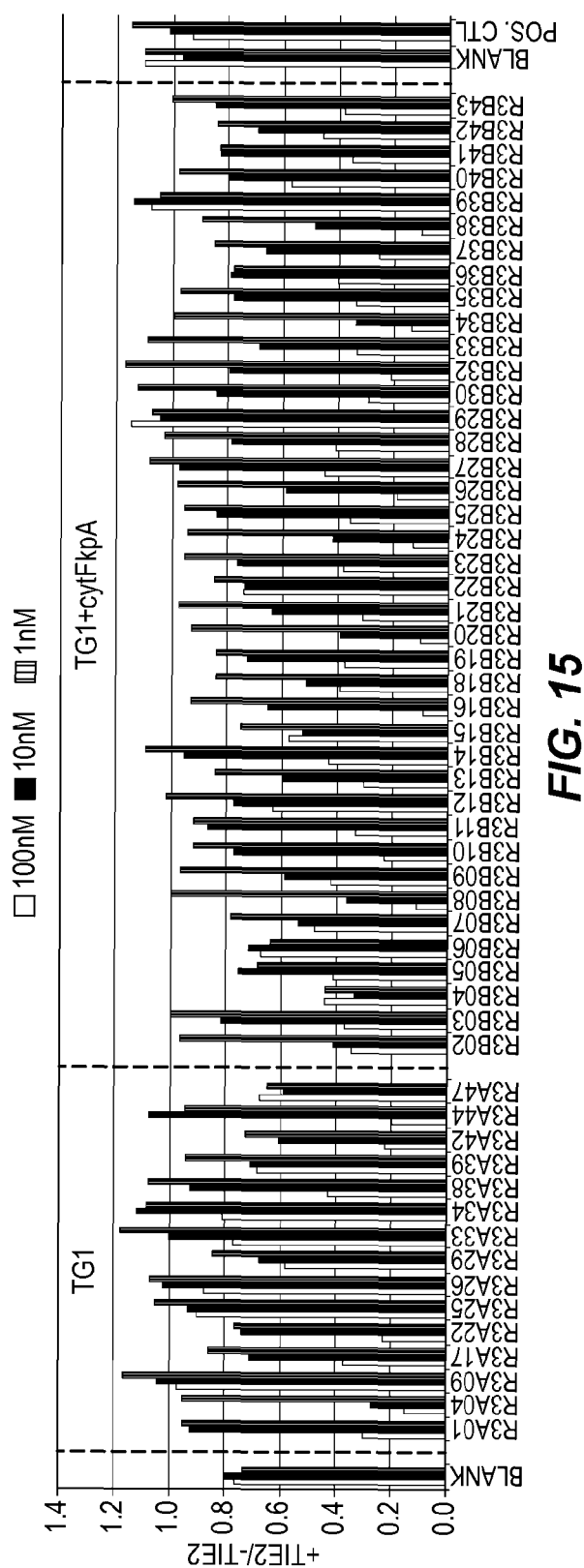
FIG. 15 illustrates the results of a competitive ELISA for unique clones selected in panning using TG1 or TG1+ cytFkpA cells during phage rescues. TIE2, 100 nM (white bars), 10 nM (grey bars) or 1 nM (black bars), was mixed with periplasmic extracts containing Fabs. Following development of the ELISA, the absorbance at 450 nm for each concentration of TIE2 was compared to the absorbance at 450 nm when no TIE2 was added to the periplasmic extracts, and expressed as a ratio.

Periplasmic extracts from the unique clones (15 from TG1 and 40 from TG1+cytFkpA) were then used in a competition ELISA. A larger percentage of clones selected in the panning with TG1+cytFkpA were still able to bind the ELISA plate in the presence of every concentration of TIE2 mixed with the periplasmic extract (FIG. 15). Expression of cytoplasmic FkpA during the panning process increases the diversity of the clones selected and this increase in diversity leads to an increase in high affinity clones selected.

Example 4 i. Cytoplasmic Expression of Fkp Increases Display of Fab Antibody Fragments on Phage One liter cultures of TG1 or TG1 harboring pAR3-FkpA_cyt (TG1+cytFkpA) each also carrying phagemids expressing XOMA libraries of Fabs with either lambda or kappa light chains were started at $OD_{600}$=0.1. These four cultures were grown with shaking at 250 rpm until the $OD_{600}$ reached 0.5 in 2YT media supplemented with 2% glucose (w/v) and 100 µg/ml carbenicillin. Chloramphenicol (34 µg/ml) was also added to the TG1+cytFkpA. The cells were then infected with M13K07 helper phage at an MOI of 20. The infection proceeded for 1 hour at 37° C.; 30 minutes without shaking and 30 minutes with shaking at 100 rpm. After infection the media was changed to 2YT supplemented with 100 µg/ml carbenicillin, 50 µg/ml kanamycin, and the TG1+cytFkpA cultures also had 34 µg/ml chloramphenicol. Samples (50 ml) were taken from each culture at 8 and 25 hours after the start of the infection with helper phage. These were centrifuged and heated to 60° C. to remove the bacteria. The phage were stored in 15% glycerol at −80° C.

Figure 16:
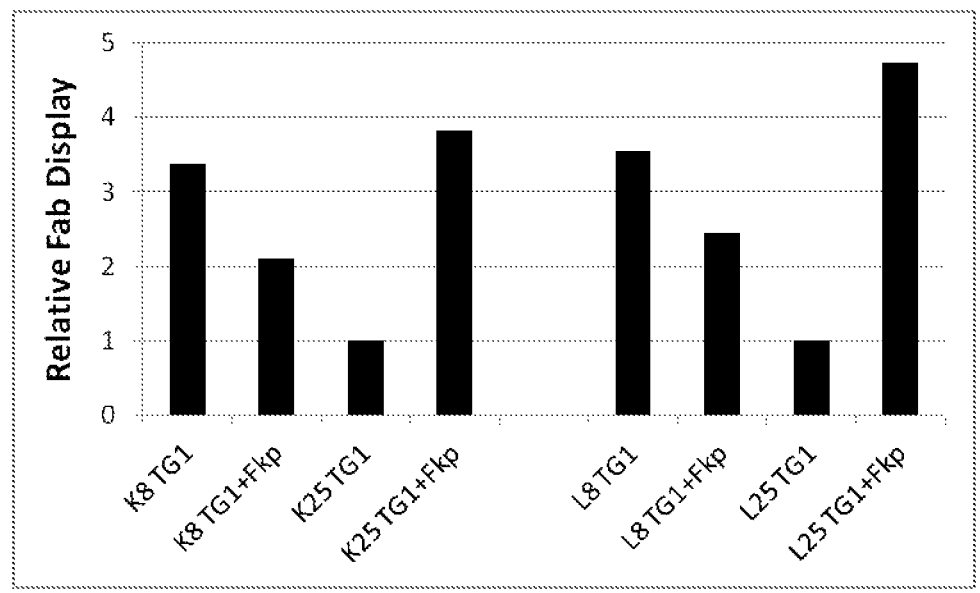
FIG. 16 illustrates the results of a relative display of kappa and lambda Fabs on phage produced in TG1 cells or TG1 cells expressing cytoplasmic FkpA. Samples were taken 8 (K8, L8) and 25 (K25, L25) hours after helper phage infection. Values are displayed relative to kappa or lambda library rescue in TG1 cells at 25 hours post-infection, respectively.

The samples taken at 8 and 25 hours were PEG precipitated to concentrate the phage. Serial dilutions of these samples were made in 3% milk in PBS and applied for 1 hour at RT to Maxisorp plates that had been coated with anti-M13 (27-9420-01, GE Healthcare) at 1:1000 dilution in PBS or anti-V5 (V-8012, Sigma-Aldrich) at 1:2000 dilution in PBS overnight at 4° C., then blocked for 1 hour at RT with 3% milk in PBS. The phage were detected with anti-M13-HRP (27-9421-01, GE Healthcare) at 1:5000 dilution in 3% milk in PBS for 1 hour at RT. The assay was developed by the addition of TMB soluble substrate (50-76-11, KPL). The reaction was quenched by the addition of 50 ul of 2 $NH_2SO_4$ and read at 450 nm by a SPECTRAMax® Plus microplate reader. The $EC_{50}$ for each set of dilutions was calculated by fitting a sigmoidal dose response curve using GraphPad Prism. The relative level of Fab display was calculated by dividing the inverse of the $EC_{50}$ from the anti-V5 ELISA, where the V5-tag indicates the presence of a Fab molecule displayed on a phage, by the inverse of the $EC_{50}$ from the anti-M13 ELISA and comparing each ratio to the ratio calculated for the 25 hour time point of the rescue in TG1 cells (FIG. 16). At the 25 hour time point, the normal time for harvest, rescues done with cytoplasmic expression of FkpA had greater than 3.5-fold more display than the library rescue without FkpA expression. Therefore, using this chaperone for phage library production increases the quality of the library.

Figure 17A:
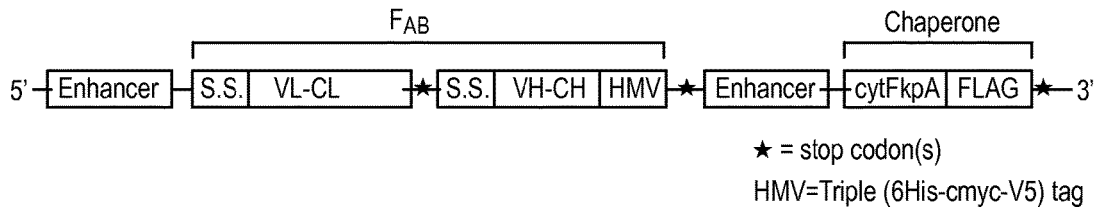
FIG. 17A is a schematic of a phagemid vector expressing the ING1 (anti-EpCAM) Fab in the *E. coli* periplasm (see Example 1) modified to replace the gene fragment encoding the M13 phage pIII protein with the cytoplasmically expressed chaperone cytFkpA (FkpA without its native signal sequence), resulting in a tricistronic plasmid expressing ING1 Fab and cytoplasmic FkpA.

Example 5 i. Construction of a Tricistronic Plasmid Expressing ING1 Fab and Cytoplasmic FkpA The phagemid vector expressing the ING1 (anti-EpCAM) Fab in the *E. coli* periplasm (see Example 1) was modified to replace the gene fragment encoding the M13 phage pIII protein with the cytoplasmically expressed chaperone cytFkpA (FkpA without its native signal sequence). Two non-amber stop codons were added downstream of the triple detection tag (6His-cmyc-V5; described in patent application number WO 2010/040073 A1). The gene fragment encoding cytFkpA was amplified by PCR from vector pAR3-FkpA_cyt (described in Example 1) together with an enhancer sequence and C-terminal FLAG tag, and cloned into the plasmid expressing the ING1 Fab to produce a tricistronic plasmid expressing ING1 Fab and cytoplasmic FkpA (FIG. 17A).

Figure 17B:
FIG. 17B is a Western blot (reduced) developed with anti-FLAG antibodies for detection of Fkp (−) from the tricistronic Fab vector described in FIG. 17A (expressed in TG1 cells).

FkpA without the periplasmic leader sequence (see (−) sign) was expressed in TG1 cells harboring a tricistronic plasmid that coexpresses cytFkpA together with the ING1 Fab (FIG. 17B). Periplasmic extracts were generated as described in Example 1, using selection without chloramphenicol (ampicillin-only) and simultaneous induction of ING1 Fab and cytFkpA using 1 mM IPTG.

Figure 17C:
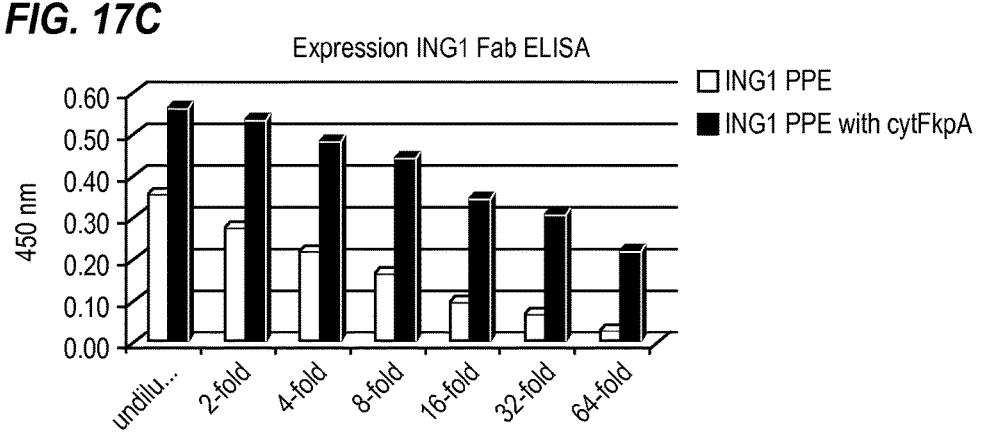
FIGS. 17C and 17D illustrate the total and functional amounts of ING1 Fab in the *E. coli* periplasm assessed by expression and target ELISAs. These results showed a substantial improvement of expression of both the total Fab level (FIG. 17C) and EpCAM-binding (FIG. 17D) upon coexpression of cytFkpA.
Figure 17D:
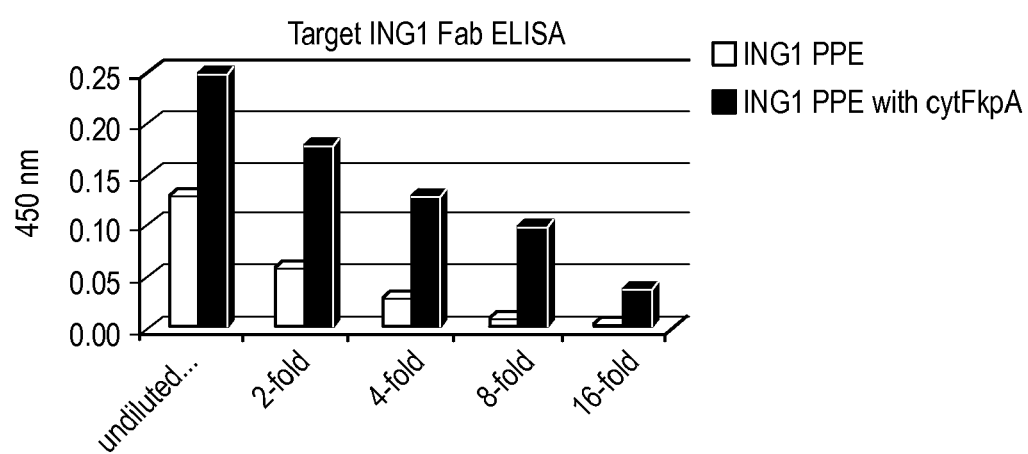

The total and functional amounts of ING1 Fab in the *E. coli* periplasm were assessed by expression and target ELISAs, as previously described. These results showed a substantial improvement of expression of both the total Fab level (see FIG. 17C) and EpCAM-binding (see FIG. 17D) upon coexpression of cytFkpA. This demonstrates the usefulness of heterologous coexpression of cytFkpA in the *E. coli* cytoplasm under the control of a single promoter in a single plasmid vector.

Periplasmic ING1 Fab yields were calculated by SPR, as described in Example 1. The SPR sensograms and a chart of the estimated protein yields based on a standard curve are shown in FIGS. 18A and 18B, respectively. In conclusion, the total yield of ING1 Fab (14.2 µg/ml) was dramatically increased upon coexpression of cytFkpA in the *E. coli* cytoplasm. The amount of active ING1 Fab bound to the antigen EpCAM and its specific activity were also calculated, as described in Example 1. FIG. 18C shows that coexpression of cytFkpA increased the amount of functional ING1 Fab. Its specific activity remained unchanged.

Example 6 i. Effect of Cytoplasmic FkpA on ING1 Fab Protein Yields from "Leaky" *E. coli* Strain CY15070

Figure 19A:
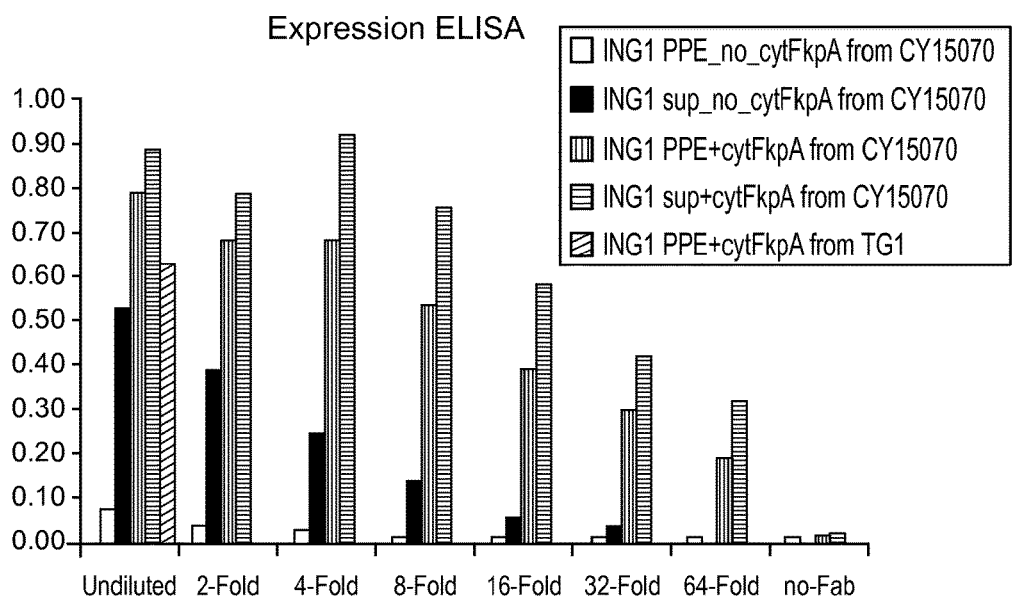
FIGS. 19A and 19B illustrate the results of an experiment using leaky *E. coli* strain CY15070 expressing ING1 Fab with or without cytoplasmic FkpA. The total amount of ING1 Fab expressed in the periplasm (FIG. 19A) and the amount of active ING1 Fab binding the ING1 target antigen EpCAM (FIG. 19B) were assessed by expression and target ELISAs, respectively. In expression ELISAs, anti-kappa coated antibodies were used to detect the Fab light chains. The Fab heavy chains were then detected by antibodies recognizing the V5 tag on the C-terminus of CH1.
Figure 19B:
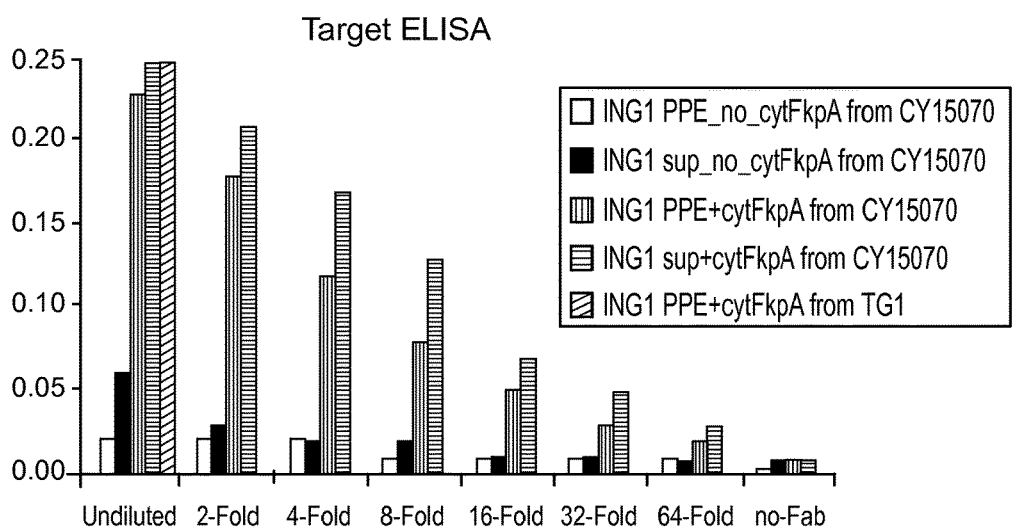

The use of *E. coli* (leaky) strains that allow the export of recombinant antibody fragments (or other proteins) into the extracellular media could obviate the need to generate periplasmic extracts. This could greatly accelerate high-throughput screening processes and reduce the cost and time of manufacture. The human light kappa anti-EpCAM ING1 Fab was expressed in the leaky strain CY15070 (Paluh et al., *Nucl. Acids Res.* 24; 14(20): 7851-60 (1986)), with or without the chaperone plasmid pAR3-FkpA_cyt. CY15070 electroporation-competent cells (ATCC#47022) were prepared according to established protocols (*Biotechniques*, 20: 42-44 (1996)) and transformed with the plasmid vector expressing ING1 Fab, either alone or together with the chaperone-expressing monocistronic vector pAR3-FkpA_cyt (vectors described in Example 1). Periplasmic extracts of CY15070 cells expressing Fabs alone or together with the cytFkpA were prepared as described in Example 1. Cell supernatants were collected following cell centrifugation. Periplasmic extracts from TG1 cells harboring the ING1 Fab and the pAR3-FkpA_cyt chaperone plasmids were used as positive controls for subsequent ELISA assays. The total amount of ING1 Fab expressed in the periplasm and the amount of active ING1 Fab binding the ING1 target antigen EpCAM were assessed by expression and target ELISAs, respectively. In expression ELISAs, anti-kappa coated antibodies were used to detect the Fab light chains. The Fab heavy chains were then detected by antibodies recognizing the V5 tag on the C-terminus of CH1 (see FIG. 19A). In target ELISAs, Fab-specific polyclonal antibodies were used to identify the functional antibodies that are able to recognize the coated EpCAM antigen (see FIG. 19B). The amount of Fab in the supernatant of CY15070 was tested by ELISA, as described in Example 1. The expression ELISA (FIG. 19A) demonstrates that the total amount of ING1 Fab found in the supernatant of CY15070, only when the Fab is coexpressed with cytoplasmic FkpA, is slightly higher than the total Fab expressed in the periplasm of TG1 cells. In the absence of this chaperone no Fab is expressed in the periplasm of CY10570, whereas some Fab can be located in the supernatant.

The target ELISA results (FIG. 19B) show that the levels of functional ING1 Fab in the CY15070 periplasm and supernatant are similar to the levels of active Fab expressed in the periplasm of TG1 cells only when coexpressed with the cytoplasmic FkpA. These findings highlight the importance of this chaperone in the folding of ING1 Fab in CY15070 E. coli cells.

What is claimed:

1. A prokaryotic host cell that expresses a heterologous protein for recombinant production comprising:
   (a) a first polynucleotide encoding (i) a sequence consisting of FkpA, or functional fragment thereof, that is not linked to a functional signal sequence, or (ii) Skp, or functional fragment thereof, that is not linked to a functional signal sequence, and
   (b) a second polynucleotide encoding the heterologous protein linked to a functional signal sequence.

2. The host cell of claim 1 wherein the host cell comprises a first polynucleotide encoding a sequence consisting of FkpA, or functional fragment thereof, that is not linked to a functional signal sequence, optionally wherein the host cell further comprises a polynucleotide encoding Skp, or functional fragment thereof, that is not linked to a functional signal sequence.

3. The host cell of claim 1 wherein the host cell comprises a first polynucleotide encoding Skp, or functional fragment thereof, that is not linked to a functional signal sequence.

4. The host cell of claim 1 wherein the prokaryotic host cell is selected from the group consisting of *Escherichia coli, Salmonella typhimurium, Bacillus subtilis, Bacillus licheniformis, Bacillus megaterium, Bacillus brevi, Pseudomonas aeruginosa, Pseudomonas fluorescens, Ralstonia eutropha, Staphylococcus carnosus* and *Serratia marcescans*.

5. The host cell of claim 1 wherein the heterologous protein is associated with mis-folding or a slow folding rate in the absence of FkpA and Skp.

6. The host cell of claim 1 wherein the heterologous protein is fused to a filamentous phage coat protein or fragment thereof.

7. The host cell of claim 1 wherein the heterologous protein is an antibody.

8. The host cell of claim 1 wherein the functional fragment of FkpA is a chaperone domain fragment.

9. The host cell of claim 8 wherein the chaperone domain fragment comprises amino acids 26-140 of SEQ ID NO: 1 or wherein the chaperone domain fragment comprises an amino acid sequence at least 75% identical to at least 100 amino acids of amino acids 26 through 140 of SEQ ID NO: 1.

10. The host cell of claim 1 wherein the functional fragment of FkpA is a peptidylprolyl isomerase domain fragment.

11. The host cell of claim 10 wherein the peptidylprolyl isomerase domain fragment comprises amino acids 141-270 of SEQ ID NO: 1 or wherein the peptidylprolyl isomerase domain fragment comprises an amino acid sequence at least 75% identical to a fragment of at least 100 amino acids of amino acids 141 through 270 of SEQ ID NO: 1.

12. The host cell of claim 3 wherein the functional fragment of Skp comprises amino acids 21-161 of SEQ ID NO: 2.

13. A plurality of cells comprising at least $10^3$ different prokaryotic host cells according to claim 1, each such host cell expressing a different heterologous protein.

14. A method for increasing recombinant production of a functional heterologous protein in a prokaryotic host cell, comprising co-expressing:
(a) a first polynucleotide encoding (i) a sequence consisting of FkpA, or functional fragment thereof, that is not linked to a functional signal sequence, or (ii) Skp, or functional fragment thereof, that is not linked to a functional signal sequence, and
(b) a second polynucleotide encoding a heterologous protein that is linked to a functional signal sequence, whereby the amount of functional heterologous protein produced is increased compared to expressing (b) in the absence of (a).

15. The method of claim 14 wherein the functional signal sequence linked to the heterologous protein directs secretion to the periplasm.

16. The method of claim 14 wherein the host cell comprises (a) a polynucleotide encoding a sequence consisting of FkpA, or a functional fragment thereof, that is not linked to a functional signal sequence, and (b) a polynucleotide encoding Skp, or functional fragment thereof, that is not linked to a functional signal sequence.

17. The method of claim 14 wherein the prokaryotic host cell is selected from the group consisting of *Escherichia coli, Salmonella typhimurium, Bacillus subtilis, Bacillus licheniformis, Bacillus megaterium, Bacillus brevi, Pseudomonas aeruginosa, Pseudomonas fluorescens, Ralstonia eutropha, Staphylococcus carnosus,* and *Serratia marcescans.*

18. The method of claim 14 wherein the heterologous protein is associated with mis-folding or a slow folding rate in the absence of FkpA and Skp.

19. The method of claim 14 wherein the heterologous protein is fused to a filamentous phage coat protein or fragment thereof.

20. The method of claim 14 wherein the heterologous protein is an antibody.

21. The method of claim 14 wherein the functional fragment of FkpA is a chaperone domain fragment.

22. The method of claim 21 wherein the chaperone domain fragment comprises amino acids 26-140 of SEQ ID NO: 1 or wherein the chaperone domain fragment comprises an amino acid sequence at least 75% identical to at least 100 amino acids of amino acids 26 through 140 of SEQ ID NO: 1.

23. The method of claim 14 wherein the functional fragment of FkpA is a peptidylprolyl isomerase domain fragment.

24. The method of claim 23 wherein the peptidylprolyl isomerase domain fragment comprises amino acids 141-270 of SEQ ID NO: 1 or wherein the peptidylprolyl isomerase domain fragment comprises an amino acid sequence at least 75% identical to a fragment of at least 100 amino acids of amino acids 141 through 270 of SEQ ID NO: 1.

25. The method of claim 14 wherein the functional fragment of Skp comprises amino acids 21-161 of SEQ ID NO: 2.

26. The host cell of claim 1 or the method of claim 14, wherein the host cell has a leaky phenotype.

27. The host cell of claim 1 or the method of claim 14, wherein the polynucleotide of (a) and the polynucleotide of (b) are operatively linked to the same regulatory control sequence.

28. The host cell of claim 1 or the method of claim 14, wherein the polynucleotide of (a) and the polynucleotide of (b) are on the same plasmid or wherein the polynucleotide of (a) and the polynucleotide of (b) are on different plasmids.

* * * * *